United States Patent
Ishihara et al.

(10) Patent No.: US 10,765,761 B2
(45) Date of Patent: Sep. 8, 2020

(54) NUCLEIC ACID CONDENSING PEPTIDE, NUCLEIC ACID CONDENSING PEPTIDE SET, NUCLEIC ACID DELIVERY CARRIER, NUCLEIC ACID DELIVERY METHOD, CELL PRODUCTION METHOD, CELL DETECTION METHOD AND KIT

(71) Applicant: KABUSHIKI KAISHA TOSHIBA, Minato-ku (JP)

(72) Inventors: Mitsuko Ishihara, Setagaya (JP); Eiichi Akahoshi, Shinagawa (JP); Emi Nozaki, Yokohama (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 0 days.

(21) Appl. No.: 16/119,738

(22) Filed: Aug. 31, 2018

(65) Prior Publication Data

US 2019/0167812 A1 Jun. 6, 2019

Related U.S. Application Data

(63) Continuation of application No. PCT/IB2017/057317, filed on Nov. 22, 2017.

(30) Foreign Application Priority Data

Nov. 22, 2016 (JP) .................. 2016-226895
Sep. 15, 2017 (JP) .................. 2017-178206

(51) Int. Cl.

| A61K 38/00 | (2006.01) |
|---|---|
| A61K 48/00 | (2006.01) |
| A61K 9/127 | (2006.01) |
| C07K 7/08 | (2006.01) |
| A61K 31/7088 | (2006.01) |
| A61P 25/00 | (2006.01) |
| A61P 9/00 | (2006.01) |
| A61P 35/00 | (2006.01) |
| A61P 3/10 | (2006.01) |
| C07K 14/00 | (2006.01) |
| A61K 41/00 | (2020.01) |
| C12N 15/113 | (2010.01) |
| C12N 15/88 | (2006.01) |
| C12Q 1/66 | (2006.01) |
| A61K 33/243 | (2019.01) |
| A61K 31/4184 | (2006.01) |
| A61K 31/575 | (2006.01) |
| A61K 38/12 | (2006.01) |

(52) U.S. Cl.
CPC .......... A61K 48/0033 (2013.01); A61K 9/127 (2013.01); A61K 31/7088 (2013.01); A61K 41/0028 (2013.01); A61K 48/005 (2013.01); A61P 3/10 (2018.01); A61P 9/00 (2018.01); A61P 25/00 (2018.01); A61P 35/00 (2018.01); C07K 7/08 (2013.01); C07K 14/001 (2013.01); C07K 14/003 (2013.01); C12N 15/113 (2013.01); C12N 15/88 (2013.01); A61K 31/4184 (2013.01); A61K 31/575 (2013.01); A61K 33/243 (2019.01); A61K 38/12 (2013.01); C07K 2319/00 (2013.01); C12Q 1/66 (2013.01)

(58) Field of Classification Search
None
See application file for complete search history.

(56) References Cited

U.S. PATENT DOCUMENTS

| 5,945,400 A | 8/1999 | Scherman et al. |
|---|---|---|
| 8,778,886 B2 | 7/2014 | Kumar-Singh et al. |
| 2002/0132990 A1 | 9/2002 | Huston et al. |
| 2007/0086981 A1 | 4/2007 | Meijer et al. |
| 2009/0305409 A1 | 12/2009 | Kogure et al. |
| 2016/0184457 A1 | 6/2016 | Kataoka et al. |

FOREIGN PATENT DOCUMENTS

| JP | 11-500431 | 1/1999 |
|---|---|---|
| JP | 2002-153288 | 5/2002 |
| JP | 2003-289871 | 10/2003 |
| JP | 2005-151908 | 6/2005 |
| JP | 2006-67891 | 3/2006 |
| JP | WO2006/101201 | 9/2006 |
| JP | 2007-535908 | 12/2007 |
| JP | 2010-537632 | 12/2010 |
| JP | WO2015/020026 | 2/2015 |
| WO | WO 02/00914 A2 | 1/2002 |

(Continued)

OTHER PUBLICATIONS

Inder M. Verma and Nikunj Somia, Gene therapy—promises, problems and prospects, Nature|vol. 389 | Sep. 18, 1997, pp. 239-242 (Year: 1997).*

(Continued)

*Primary Examiner* — Thomas S Heard

(74) *Attorney, Agent, or Firm* — Oblon, McClelland, Maier & Neustadt, L.L.P.

(57) ABSTRACT

According to one embodiment, a nucleic acid condensing peptide includes one terminal having a first sequence RRRRRR and another terminal having a second sequence RQRQR. Between the first sequence and the second sequence, none or one or more intermediate sequences each consisting of RRRRRR or RQRQR are included. Further, of the first sequence, the second sequence and the intermediate sequences, two or more neutral amino acids are included between any two sequences adjacent to each other.

44 Claims, 14 Drawing Sheets
Specification includes a Sequence Listing.

(56) References Cited

FOREIGN PATENT DOCUMENTS

WO    WO 2011/087804 A2    7/2011

OTHER PUBLICATIONS

Gonçalves, G.A.R., Gene therapy: advance, challenges and perspectives, Einstein. 2017;15(3):369-75 (Year: 2017).*
International Search Report dated Mar. 20, 2018 in PCT/IB2017/057317, filed on Nov. 22, 2017.
Written Opinion dated Mar. 20, 2018 in PCT/IB2017/057317, filed on Nov. 22, 2017.
Bremner, K., et al. "Factors Influencing the Ability of Nuclear Localization Sequence Peptides to Enhance Nonviral Gene Delivery", Bioconjugate Chemistry, vol. 15, No. 1, 203, pp. 152-161.
Mann, A., et al. "Linear Short Histidine and Cysteine Modified Arginine Peptides Constitute a Potential Class of DNA Delivery Agents", molecular pharmaceutics, vol. 11, No. 3, 2014, pp. 683-696.
Brewer, L., et al. "Dynamics of Protamine 1 Binding to Single DNA Molecules", The Journal of Biological Chemistry, vol. 278, No. 43, 2003, pp. 42403-42408.
Jung, J., et al. "Bio-nanocapsule conjugated with liposomes for in vivo pinpoint delivery of various materials", Journal of Controlled Release, vol. 126, No. 3, 2007, pp. 255-264.
Schwartz, B., et al. "Synthetic DNA-compacting peptides derived from human sequence enhance cationic lipid-mediated gene transfer in vitro and in vivo", Gene Therapy, vol. 6, 1999, pp. 282-292.
Siomi, H., et al. "A Nuclear Localization Domain in the hnRNP A1 Protein", The Journal of Cell Biology, vol. 129, No. 3, 1995, pp. 551-560.
Subramanian, A., et al. "Nuclear targeting peptide scaffolds for lipofection of nondividing mammalian cells", Nature Biotechnology, vol. 17, 1999, pp. 873-877.

* cited by examiner

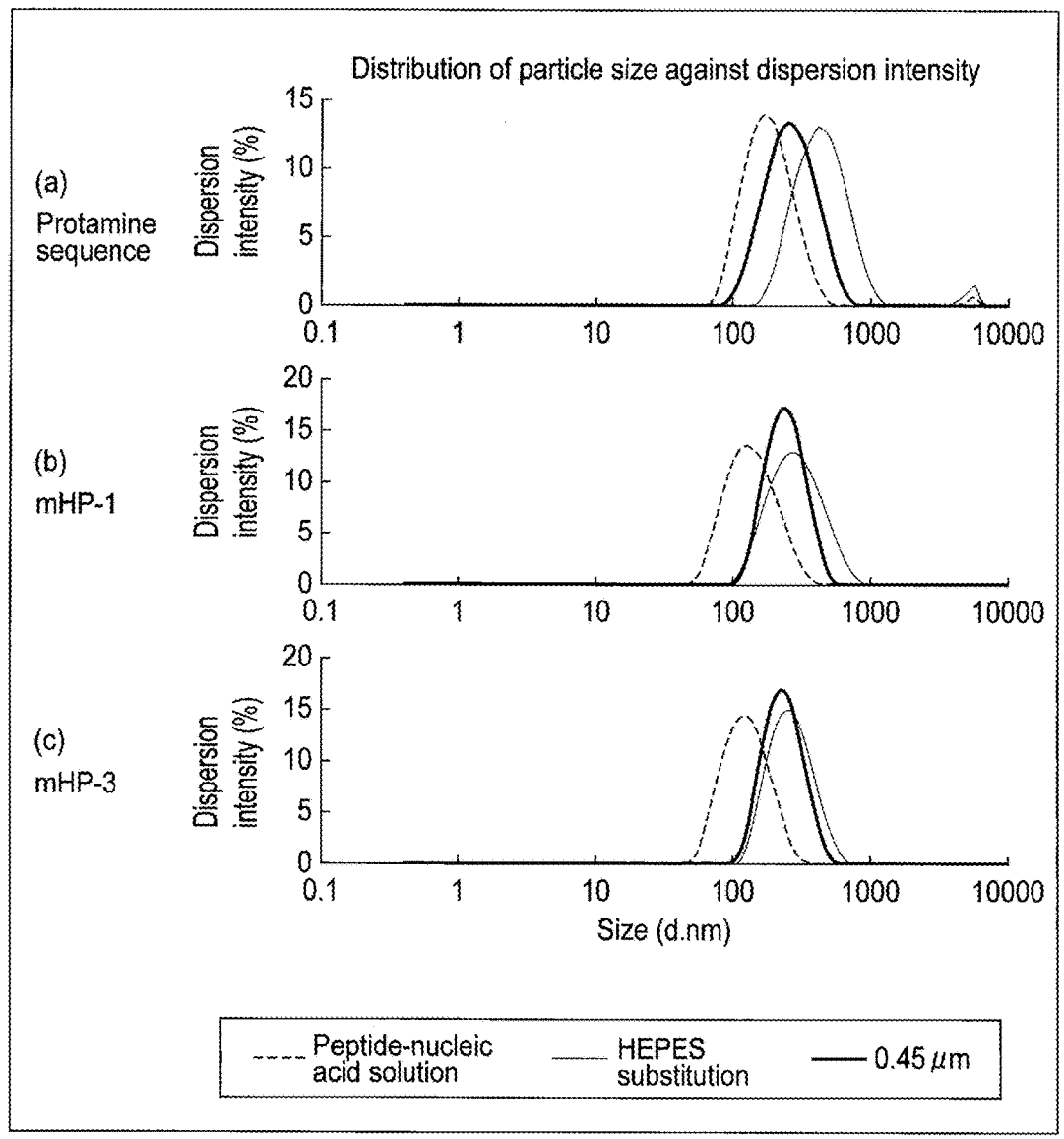
F I G. 7

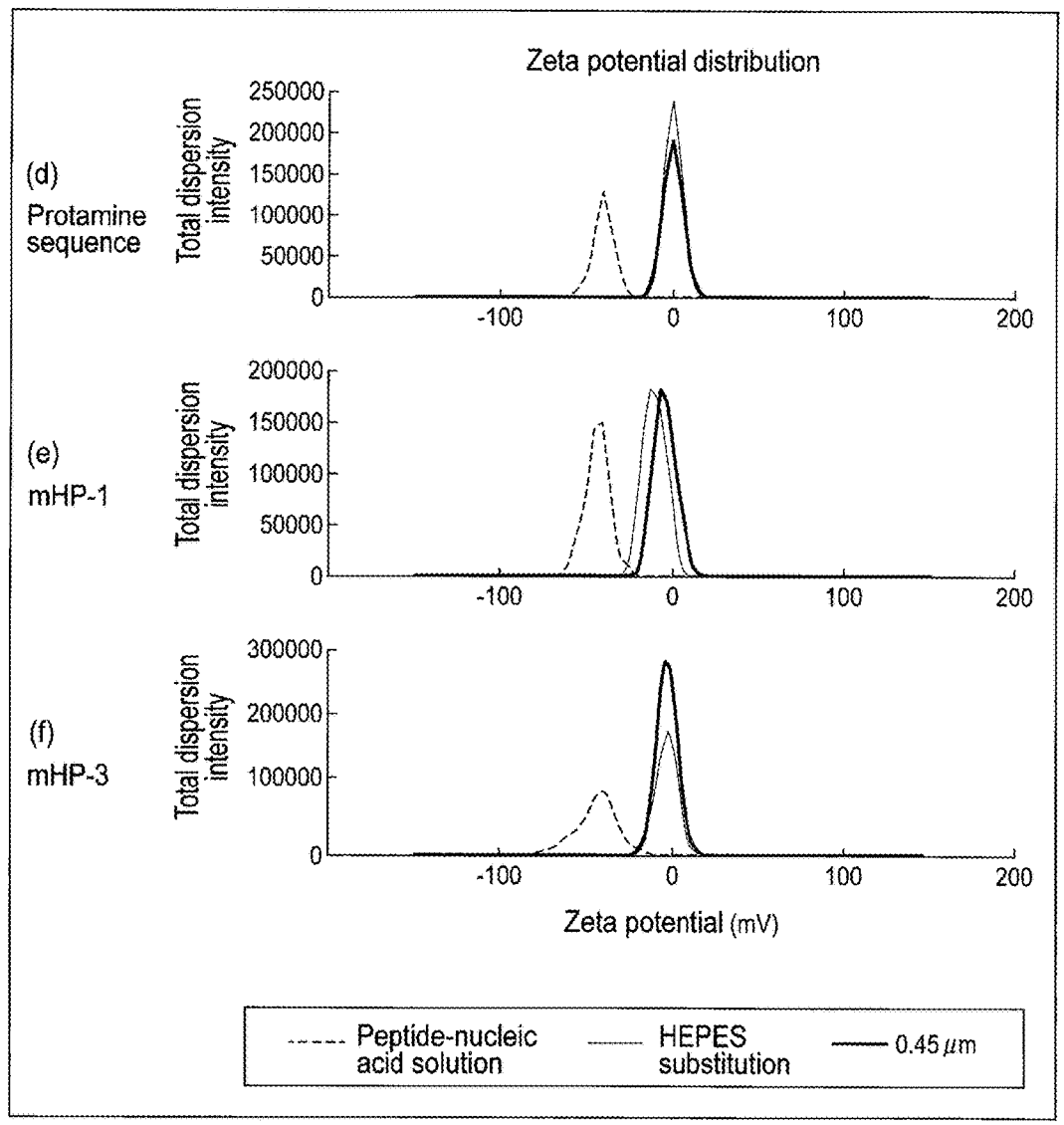
F I G. 8

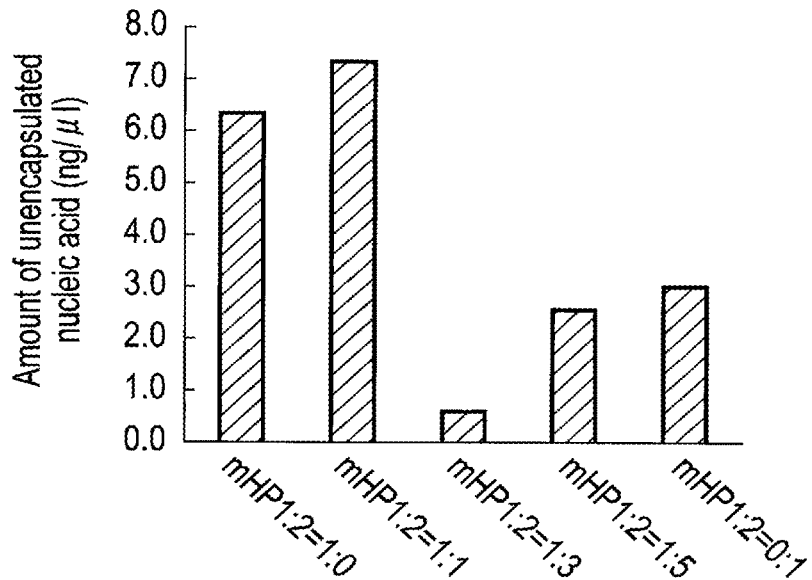
F I G. 12
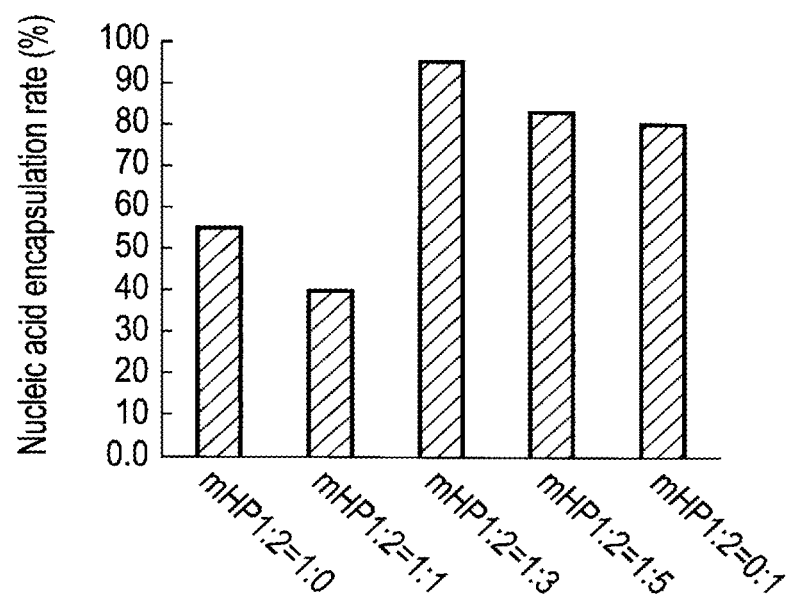
F I G. 13

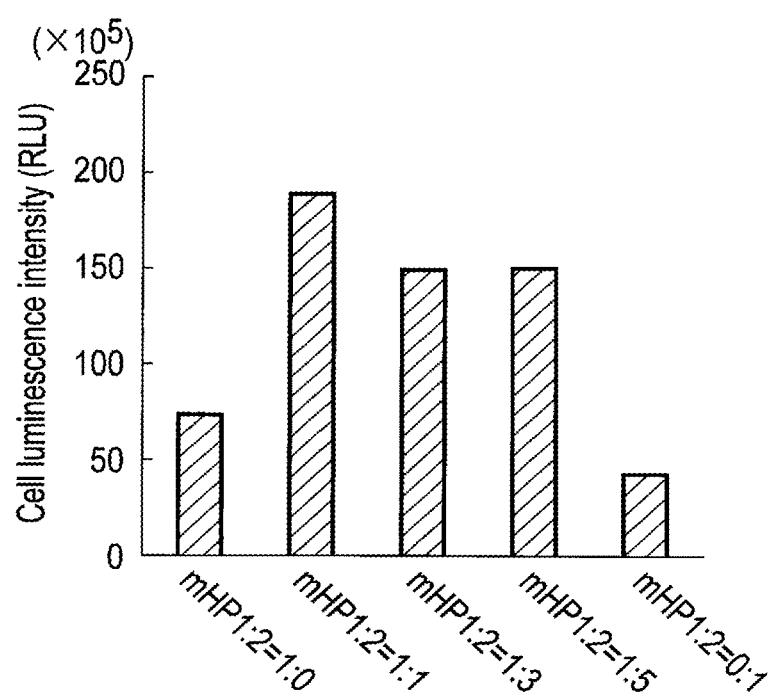
F I G. 14

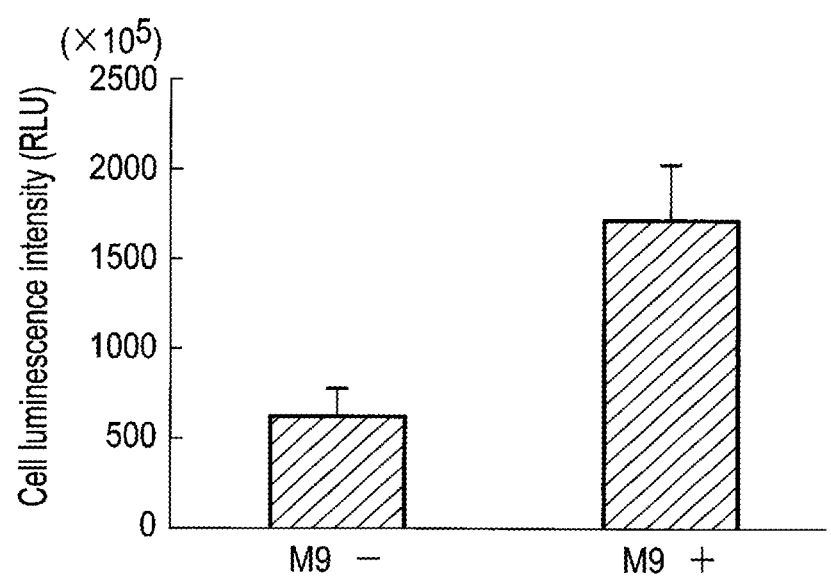
F I G. 16

NUCLEIC ACID CONDENSING PEPTIDE, NUCLEIC ACID CONDENSING PEPTIDE SET, NUCLEIC ACID DELIVERY CARRIER, NUCLEIC ACID DELIVERY METHOD, CELL PRODUCTION METHOD, CELL DETECTION METHOD AND KIT

CROSS-REFERENCE TO RELATED APPLICATIONS

This application is a Continuation Application of PCT Application No. PCT/IB2017/057317, filed Nov. 22, 2017 and based upon and claiming the benefit of priority from Japanese Patent Applications No. 2016-226895, filed Nov. 22, 2016; and No. 2017-178206, filed Sep. 15, 2017, the entire contents of all of which are incorporated herein by reference.

FIELD

Embodiments described herein relate generally to a nucleic acid condensing peptide, a nucleic acid condensing peptide set, a nucleic acid delivery carrier, a nucleic acid delivery method, a cell production method, a cell detection method and a kit therefor.

BACKGROUND

In recent years, in such fields as gene therapy and genetic screening, technologies of delivering small molecules such as nucleic acids to a cell are being actively developed. An example of the method of delivering nucleic acid to a cell is such that nucleic acid is encapsulated in a lipid membrane such as liposome, and delivering the nucleic acid to the cell by endocytosis or the like. As a liposome used to deliver nucleic acid into a cell, cationic liposome is studied and its application is progressing. Cationic liposome is a liposome comprising lipid having cationic properties and an auxiliary lipid which stabilizes the membrane, and is accumulated nonspecifically a cell membrane anionically charged. However, since nucleic acid is anionic and therefore sticks to a surface of a cationic liposome when encapsulating the nucleic acid in the liposome, it is difficult to encapsulate nucleic acid solely into a liposome. Here, in order to encapsulate nucleic acid into a liposome efficiently, a technique which binds nucleic acid with a peptide or the like and then encapsulated into a liposome is often used.

Under these circumstances, there is a demand of further development of the peptide which can encapsulate nucleic acid in a liposome more efficiently, and further development of the method delivering nucleic acid more efficiently to a cell.

BRIEF DESCRIPTION OF THE DRAWINGS

FIG. 7 is a graph showing test results of Example 3.

FIG. 8 is a graph showing test results of Example 3.

FIG. 12 is a graph showing test results of Example 9.

FIG. 13 is a graph showing test results of Example 9.

FIG. 14 is a graph showing test results of Example 10.

FIG. 16 is a graph showing test results of Example 14.

DETAILED DESCRIPTION

In general, according to one embodiment, a nucleic acid condensing peptide is a peptide which condenses nucleic acid. The peptide comprises a terminal having a first sequence RRRRRR and another terminal having a second sequence RQRQR. Between the first sequence and the second sequence, there may be none or one or more intermediate sequences of RRRRRR or RQRQR contained. Further, of the first sequence, the second sequence and the intermediate sequences, a plurality of neutral amino acids are contained between any two sequences adjacent to each other.

Various embodiments will be described below with reference to the accompanying drawings. Further, the drawings are schematic diagrams designed to assist the reader to understand the embodiments easily. Thus, there may be sections where the shape, dimensions, ratio, etc., are different from those of the actual devices, but they can be re-designed as needed with reference to the following explanations and publicly known techniques.

1. Outline

Figure 1:
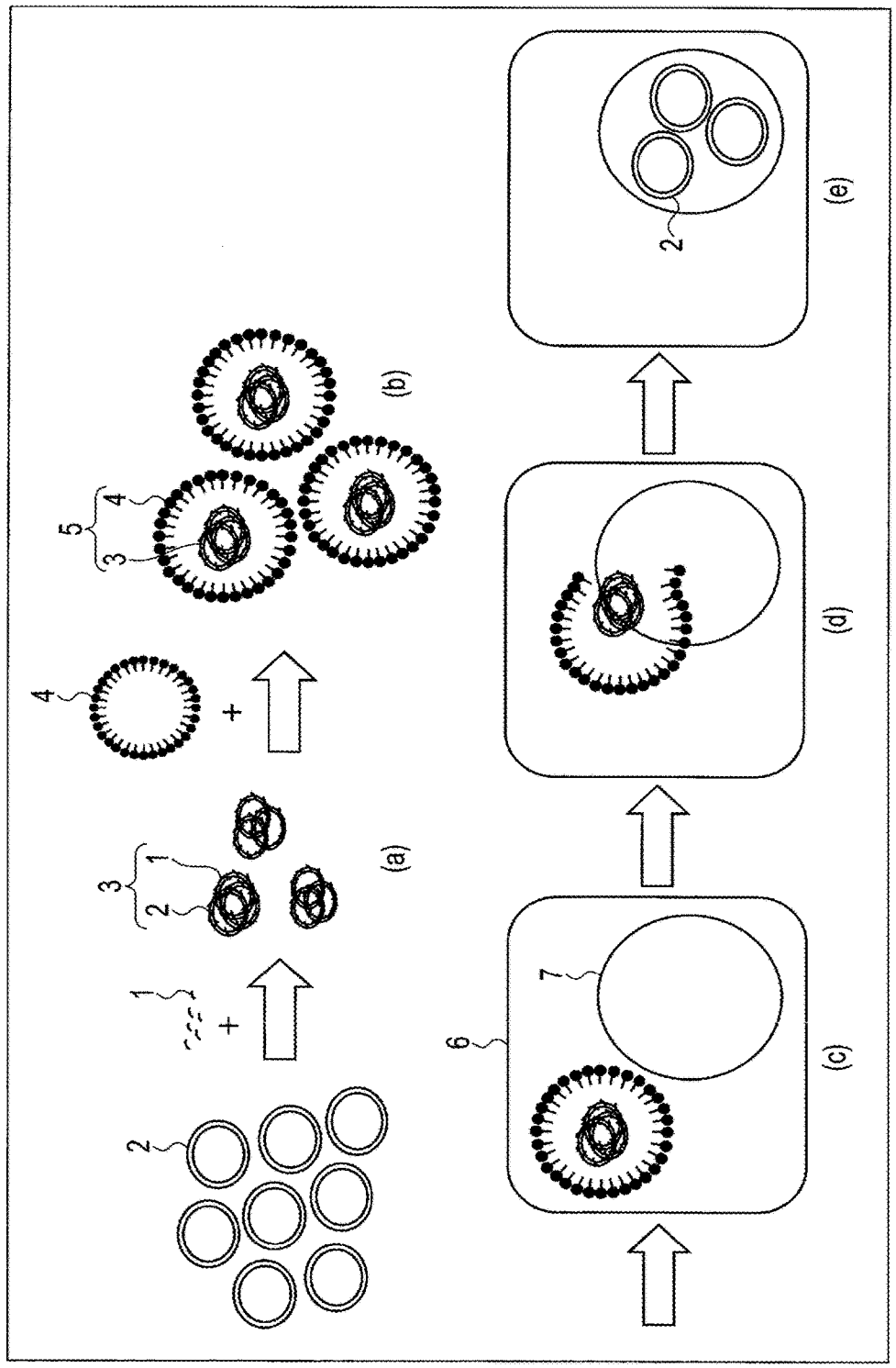
FIG. 1 is a schematic diagram showing the situation of an example in which a nucleic acid condensing peptide of an embodiment is used.

The nucleic acid condensing peptide according to the embodiment is a peptide which condenses nucleic acid. The nucleic acid condensing peptide is used, for example, as follows. FIG. 1 shows an example of use of the nucleic acid condensing peptide.

When nucleic acid condensing peptide 1 is brought into contact with nucleic acid 2, the nucleic acid 2 is condensed to form a complex 3 (process (a) of FIG. 1). Then, the complex 3 is encapsulated in a nucleic acid delivery membrane 4, and thus a nucleic acid delivery carrier 5 is acquired (process (b)). The nucleic acid delivery carrier 5 is transfected into a cell 6 (process (c)). When the nucleic acid delivery carrier 5 is transfected into the cell 6, the nucleic acid delivery membrane 4 cleaves to release the complex 3 out of the nucleic acid delivery membrane 4 (process (d)). Then, the nucleic acid 2 is dissociated from the nucleic acid condensing peptide 1 and the nucleic acid 2 is transfected into a nucleus 7 (process (e)). In this manner, the nucleic acid 2 is efficiently delivered to the cell 6.

According to the embodiments, a nucleic acid condensing peptide, a nucleic acid condensing peptide set containing the nucleic acid condensing peptide, a nucleic acid delivery carrier, a nucleic acid delivery method, a cell production method, a cell detection method and a kit thereof can be provided. The details of these will be described.

2. Nucleic Acid Condensing Peptide

The nucleic acid condensing peptide is a peptide which condenses nucleic acid.

The nucleic acid may be DNA or RNA. The nucleic acid may be, for example, circular or linear. In the case of circular, the nucleic acid may be, for example, a plasmid vector. In the case of linear, the nucleic acid may be, for example, a linear DNA, miRNA, siRNA, mRNA or the like.

The nucleic acid may contain a conventionally known gene expression cassette which expresses a target gene, for example. The gene expression cassette may contain, for example, a base sequence which codes one or more target genes expressible in a cell when the nucleic acid is transfected into the cell. The target gene may be, for example, a gene for producing a target protein, RNA or the like. The target gene may be, for example, a gene for modifying the function of a cell, a gene for leading a cell to apoptosis, a reporter gene, a gene for making a cell to produce a desired substance or the like.

The gene for modifying the function of a cell may be, for example, a gene for adding new cell function, a gene for compensating for weakened or lost normal cell function, a gene which suppresses a harmful effect in cell, a gene for differentiating a cell or the like.

The gene for adding new cell function or the gene for compensating for weakened or lost normal cell function or gene which suppresses a harmful effect in cell may be, for example, a gene used to prevent, remedy or treat diseases such as cancers, psychiatric disorders, lifestyle-related diseases, neurological diseases, autoimmune diseases, and cardiovascular disease in the field of gene therapy and the like. Usable examples of such a gene are P53 gene, TCR gene and CAR gene.

The gene for differentiating a cell may be, for example, a gene to be transfected into a stem cell to differentiate the stem cell into a cell having a desired function in the field of regenerative medicine and the like. Usable examples of such a gene are OCT3/4 gene, Sox2 gene, Klf4 gene, cMyc gene, Runx2 gene, STAT3 gene, or Nanog gene.

The gene for leading a cell to apoptosis may be, for example, a gene used in order to kill the cells of the lesion or focus of diseases such as cancer, psychiatric disorder, lifestyle-related disease, neurological disease, autoimmune disease and cardiovascular disease in the field of gene therapy and the like. Usable examples of such a gene are diphtheria toxin gene and bax gene.

The reporter gene is a gene which varies its occurrence/non-occurrence or quantity of expression with the characteristics of a cell. The characteristics of a cell may be a status as to, for example, whether or not a specific gene may be expressed in the cell, or whether the cell is normal or abnormal. The abnormal cell may be a cell affected by a specific disease. Examples of the specific disease may be cancer, psychiatric disorder, lifestyle-related disease, neurological disease, autoimmune disease and cardiovascular disease, or may be a pre-disease state, for example, a precancerous state, a prediabetic state, or the like.

The reporter gene may be a gene which expresses a reporter protein. The reporter gene may be, for example, luciferase gene, β-galactosidase gene, nitric oxide synthetase gene, xanthine oxidase gene, blue fluorescence protein gene, green fluorescence protein gene, red fluorescence protein gene, or heavy metal-binding protein gene.

The gene for making a cell to produce a desired substance may be, for example, a gene which codes the desired substance to be produced by the cell or a gene which codes a substance required for the cell to produce the desired substance. Usable examples of such a gene are insulin gene, growth hormone gene and interferon gene.

The gene expression cassette may include an expression control sequence to express a target gene in addition to the target gene itself. The gene expression cassette may contain, for example, a promoter as an expression control sequence.

A promoter may be functionally bonded to and located in upstream of the target gene. Thereby, if the characteristics of a cell to which a nucleic acid is transfected include such a condition that activates the promoter, the target gene may be expressed. That is, the characteristics of the cell can be reflected by the existence/non-existence or quantity of the target gene.

The promoter may be an endogenous or exogenous promoter.

In the case where the target gene is a reporter gene and whether or not a specific nucleic acid is transfected into the cell should be judged, the promoter may be an exogenous promoter. The exogenous promoter may be, for example, cytomegalovirus (CMV) promoter, simian virus 40 (SV40) promoter, herpes simplex virus thymidine kinase gene promoter, a Minimal promoter of any of these or an artificially synthesized promoter.

In the case where the target gene is a reporter gene and whether a cell is a normal or abnormal cell should be judged, the promoter should preferably be endogenous and be of such a type with which the characteristics of the cell can be determined based on the intensity of its activity. In that case, the intensity of the promoter activity is reflected in the amount of the reporter gene expression, and the characteristics of the cell can be determined by the amount of the expression. Such a promoter may be, for example, CK19 promoter, Ki67 promoter or nicotinamide phosphoribosyl-trasferase (NAMPT) promoter.

The gene expression cassette should preferably further include some other expression control sequence. The other expression control sequence may contain, for example, an enhancer, polyadenylated sequence, and/or any control sequence used to suppress or promote the expression.

The nucleic acid may contain a plurality of gene expression cassettes.

The nucleic acid may further contain a gene expression cassette for selecting a cell into which nucleic acid is transfected, after a nucleic acid delivery carrier is brought into contact with the cell. Such a gene expression cassette is, for example, a gene expression cassette whose target gene is a drug-resistant gene, a reporter gene or the like.

Condensing of nucleic acid means, for example, to compress nucleic acid to reduce the entire volume and/or to integrate a plurality of nucleic acids. The nucleic acid condensing peptide of the embodiment can, for example, bind to a spiral crevice of an anionic nucleic acid and contract the crevice to condense the nucleic acid.

The nucleic acid condensing peptide comprises one terminal having the first sequence RRRRRR and another terminal having the second sequence RQRQR. The alphabets used here to represent the sequences of peptides are those generally used for representing amino acids each by one character. Therefore, R refers to arginine and Q for glutamine.

For example, the first sequence may be located in an N-terminal side and the second sequence may be located in a C-terminal side, or reversely, the second sequence may be located in the N-terminal side and the first sequence on the C-terminal side.

By comprising the first and second sequences, the nucleic acid condensing peptide becomes cationic. With the cationic properties, it is possible to condense nucleic acid efficiently, and further neutralize anionic properties of the condensed nucleic acid, and encapsulate the nucleic acid into a nucleic acid delivery carrier efficiently.

In particular, when the nucleic acid condensing peptide includes the second sequence, the cationic degree of the nucleic acid condensing peptide is suppressed, and the nucleic acid condensing peptide exhibits an appropriate degree of the cationic properties as a whole. Thus, it is possible to homogenously and stably condense nucleic acid, and dissociate the nucleic acid efficiently after being delivered into a cell.

Between the first sequence and the second sequence, an intermediate sequence comprising RRRRRR or RQRQR may be included. One or more intermediate sequences may be included a nucleic acid condensing peptide, or may not necessarily be included.

When two or more intermediate sequences are included, all of them may be RRRRRR, or RQRQR, or may include both RRRRRR and RQRQR. When both are included, the order may be arbitrary and is not particularly limited.

Of the first sequence, the second sequence and the intermediate sequences, between an adjacent pair of two sequences, a sequence comprising neutral amino acids is included. The neutral amino acids are amino acids which are neutral. Such a sequence contains two or more neutral amino acids. It is preferable that 2 to 5 neutral amino acids be contained. The neutral amino acids should preferably include glycine (G) or tyrosine (Y). When two or more neutral amino acids are included, it is considered to be easy to take such a structure that nucleic acid condensing peptide binds to nucleic acid.

For example, in the case where no intermediate sequence is included in the nucleic acid condensing peptide, one region where the two or more neutral amino acids are located (which will be referred to as "neutral amino acid region" hereafter) is located between the first sequence and the second sequence in the sequence of the nucleic acid condensing peptide. In the case where one intermediate sequence is included, two neutral amino acid regions are located, more specifically, one between the first sequence and the intermediate sequence and another one between the second sequence and the intermediate sequence. In the case where two or more intermediate sequences are included, regions are located not only between the first sequence and the intermediate sequence and between the second sequence and the intermediate sequence, but also between each adjacent pair of two intermediate sequences.

Two or more neutral amino acids included in one neutral amino acid region may all be the same amino acids, or those different from each other. When three or more neutral amino acids are included in one neutral amino acid region, amino acids of the same kind or different kinds may be intermingled therein.

Further, in the case where a plurality of neutral amino acid regions exist in the sequence of a nucleic acid condensing peptide, the number and kinds of neutral amino acids included in the neutral amino acid regions may differ from each other or may be the same among the neutral amino acid regions.

The full length of the nucleic acid condensing peptide should preferably be, for example, 55 or less amino acids. With the length in this range, nucleic acid is condensed efficiently to be easily encapsulated in a nucleic acid delivery carrier, which will be described later.

The nucleic acid condensing peptide should preferably contain R at a ratio of 45% or more to the entire sequence. With the R contents at this ratio, the nucleic acid condensing peptide exhibits cationic properties, which improves the efficiency of condensing nucleic acid and the efficiency of encapsulating nucleic acid in a nucleic acid delivery carrier.

In a further embodiment, the nucleic acid condensing peptide may be composed of salts containing sulfate ion. When the nucleic acid condensing peptide is composed of salts containing sulfate ion, the amount of expression of nucleic acid in the cell is improved, which is preferable.

Such nucleic acid condensing peptide may be peptide which comprises the sequence of, for example, SEQ ID NO:1 or SEQ ID NO:2 below.

(SEQ ID NO: 1)
RQRQRYYRQRQRGGRRRRRR (mHP-1)

(SEQ ID NO: 2)
RQRQRGGRRRRRR (mHP-3)

According to such nucleic acid condensing peptide, nucleic acid can be condensed efficiently. Further, the anionic properties of nucleic acid can be weakened. Therefore, for example, nucleic acid can be encapsulated in a nucleic acid delivery membrane efficiently. Further, the nucleic acid condensing peptide dissociates nucleic acid efficiently in a cell. Therefore, if the nucleic acid condensing peptide is used, the nucleic acid transfected into a cell can be expressed efficiently in the cell.

3. Nucleic Acid Condensing Peptide Set

According to an embodiment, a nucleic acid condensing peptide set is provided.

A nucleic acid condensing peptide set contains the nucleic acid condensing peptide described above (to be referred to as the "first nucleic acid condensing peptide" hereafter), and a second nucleic acid condensing peptide and/or a third nucleic acid condensing peptide. More specifically, the nucleic acid condensing peptide set may contain the first nucleic acid condensing peptide and the second nucleic acid condensing peptide, or the first nucleic acid condensing peptide and the third nucleic acid peptide, or the first nucleic acid condensing peptide, the second nucleic acid condensing peptide and the third nucleic acid condensing peptide.

Now, the second and third nucleic acid condensing peptides will be described.

The second nucleic acid condensing peptide is a peptide for condensing nucleic acid, and comprises a third sequence at one terminal and a fourth sequence at another terminal. The third sequence and the fourth sequence are both RRRRRR. Here, R represents arginine.

The second nucleic acid condensing peptide includes none or one or more of intermediate sequences comprising RRRRRR or RQRQR between the third sequence and the fourth sequence. In other words, one or a plurality of intermediate sequences may be included in the second nucleic acid condensing peptide, or may not be included. When two or more intermediate sequences are included, the intermediate sequences may be all RRRRRR or RQRQR, or may include both RRRRRR and RQRQR. When both are included, the order may be arbitrary and is not particularly limited. Here, Q represents glutamine.

Among the third sequence, the fourth sequence and the intermediate sequences, two or more neutral amino acids are included between each adjacent pair of two sequences. The neutral amino acids may be the same as any of those described above. When two to five neutral amino acids are included, it is easy to take such a structure that is bonded to nucleic acid, which is more preferable.

For example, in the case where no intermediate sequence is included in the second nucleic acid condensing peptide, one region where neutral amino acids are located or a neutral amino acid region is located between the third sequence and the fourth sequence in the sequence of the second nucleic acid condensing peptide. In the case where one intermediate sequence is included, one neutral amino acid region is located between the third sequence and the intermediate sequence, and another neutral amino acid region is located between the fourth sequence and the intermediate sequence. In the case where two or more intermediate sequences are included, regions are located not only between the third sequence and the intermediate sequence and between the fourth sequence and the intermediate sequence, but also between each adjacent pair of two intermediate sequences.

The neutral amino acids included in one neutral amino acid region may all be the same amino acids, or different kinds of amino acids may be intermingled therein.

Further, in the case where a plurality of neutral amino acid regions exist in the sequence of a nucleic acid condensing peptide, the number and kinds of neutral amino acids included in the neutral amino acid regions may differ from each other or may be the same among the neutral amino acid regions.

The full length of the nucleic acid condensing peptide should preferably be, for example, 55 or less amino acids. With the length in this range, nucleic acid is condensed efficiently to be easily encapsulated in a nucleic acid delivery carrier.

The nucleic acid condensing peptide should preferably contain R at a ratio of 60% or more to the entire sequence. With the R contents at this ratio, the nucleic acid condensing peptide exhibits cationic properties, which improves the efficiency of condensing nucleic acid and the efficiency of encapsulating nucleic acid in a nucleic acid delivery carrier.

The second nucleic acid condensing peptide may be composed of salts containing sulfate ion. The second nucleic acid condensing peptide may be composed of salts containing sulfate ion, for example, at the C-terminal side. When the second nucleic acid condensing peptide is composed of salts containing sulfate ion, the amount of expression of nucleic acid in the cell improves, which is preferable.

The second nucleic acid condensing peptide should preferably be a peptide comprising, for example, a sequence represented by SEQ ID NO: 3 below.

```
                                            (SEQ ID NO: 3)
RRRRRRYYRQRQRGGRRRRRR (mHP-2)
```

Here, Y represents tyrosine and G represents glycine.

With the structure described above, the second nucleic acid condensing peptide has strong cationic properties at both terminals and high affinity with nucleic acid. Therefore, with use of the nucleic acid condensing peptide set containing the second nucleic acid condensing peptide, nucleic acid can be condensed still more efficiently than that of the case where the second nucleic acid condensing peptide is not used. Thus, more nucleic acids can be encapsulated in a nucleic acid delivery carrier. As a result, the amount of the nucleic acid remaining outside the nucleic acid delivery carrier is reduced. The nucleic acid remaining outside the nucleic acid delivery carrier is the nucleic acid which has not been condensed by the nucleic acid condensing peptide, or that dissociated from the nucleic acid condensing peptide after even condensed. Such nucleic acid remaining outside nucleic acid delivery carriers causes aggregation of nucleic acid delivery carriers. Therefore, with use of the nucleic acid condensing peptide set described above, aggregation of nucleic acid delivery carriers can be prevented, and therefore the nucleic acid delivery carriers do not form a large aggregate, making it easy to be transfected the nucleic acid delivery carrier into a cell. Thus, with use of the second nucleic acid condensing peptide, it is possible to transfect even more nucleic acids into a cell with higher efficiency.

In addition, after the nucleic acid delivery carriers enter a cell, the nucleic acids dissociate easily from the peptides by the action of the first nucleic acid condensing peptide. Therefore, when the nucleic acid condensing peptide set containing the second nucleic acid condensing peptide is used, the nucleic acid can be expressed in a cell still more efficiently.

The third nucleic acid condensing peptide is a peptide comprising of one M9 domain of hnRNP A1, which is an RNA-binding protein, and comprises, for example, an amino acid sequence represented by SEQ ID NO: 6, below.

```
                                            (SEQ ID NO: 6)
GNQSSNFGPMKGGNFGGRSSGPYGGGGQYFAKPRNQGGY (M9)
```

Here, G represents glycine, N for asparagine, Q for glutamine, S for serine, F for phenylalanine, P for proline, M for methionine, K for ricin, R for arginine, Y for tyrosine and A for alanine.

The third nucleic acid condensing peptide having the structure described above can further condense a complex. Therefore, with use of the third nucleic acid condensing peptide, nucleic acid can be condensed still more efficiently. Thus, it is possible to obtain nucleic acid delivery carriers having even less particle diameters. Such nucleic acid delivery carriers can be easily taken into a cell, and therefore nucleic acid can be transfected into a cell more efficiently. In addition, after nucleic acid delivery carriers enter a cell, the nucleic acids dissociate easily from the peptides by the action of the first nucleic acid condensing peptide. Thus, with use of the nucleic acid condensing peptide set of the embodiment, nucleic acid can be expressed in a cell still more efficiently.

The third nucleic acid condensing peptide may be linked to the first nucleic acid condensing peptide and/or the second nucleic acid condensing peptide contained in the nucleic acid condensing peptide set. The expression "link to" means the state that the C-terminal of one peptide and the N-terminal of the other peptide form a peptide bond. When two peptides link to each other, the two peptides may be linked, for example, via 1 to 10 amino acids. Such amino acids are, for example, glycine, cysteine or the like. In this case, when the first and/or the second nucleic acid condensing peptides linked to the third nucleic acid condensing peptide bond to nucleic acid, the third nucleic acid condensing peptide can be easily brought into contact with the complex, and therefore the above-described effect can be easily exhibited.

To one terminal of the third nucleic acid condensing peptide, an arbitrary amino acid sequence may be linked. The arbitrary amino acid sequence should preferably be an amino acid sequence which binds to the nucleic acid contained in a nucleic acid delivery carrier. Usable examples of such sequence are signal sequences such as nuclear localization signal (NLS) and the like. When the amino acid sequence capable of binding to the nucleic acid is linked to the third nucleic acid condensing peptide, the third nucleic acid condensing peptide can be easily brought into contact with the complex, and therefore the above-described effect of the third nucleic acid condensing peptide can be more easily exhibited. When the sequence capable of binding to the nucleic acid is not linked to the third nucleic acid condensing peptide, it is considered that the third nucleic acid condensing peptide is attracted to the complex with electrostatic force and thus the effect of the third nucleic acid condensing peptide can be exhibited.

In the case where the first nucleic acid condensing peptide and the second nucleic acid condensing peptide are included in the nucleic acid condensing peptide set, the first nucleic acid condensing peptide and the second nucleic acid condensing peptide should preferably be included at a ratio of 1:1 to 1:5. In this case, it is possible to express nucleic acid in a cell more efficiently. Furthermore, a further preferable ratio is 1:3.

In the case where the first nucleic acid condensing peptide and the third nucleic acid condensing peptide are contained in the nucleic acid condensing peptide set, the first nucleic acid condensing peptide and the third nucleic acid condensing peptide should preferably be contained at a ratio of 1:0.1 to 1:0.8. In this case, it is possible to express nucleic acid in a cell more efficiently. A further preferable ratio is 1:0.2.

In the case where the first nucleic acid condensing peptide, the second nucleic acid condensing peptide and the third nucleic acid condensing peptide are contained in the nucleic acid condensing peptide set, the first nucleic acid condensing peptide, the second nucleic acid condensing peptide and the third nucleic acid condensing peptide should preferably contained at a ratio of, for example, 1:1:0.1 to 1:1:0.8, or 1:3:0.1 to 1:3:0.8, and a still more preferable ratio is 1:3:0.2. When the first nucleic acid condensing peptide, the second nucleic acid condensing peptide and the third nucleic acid condensing peptide are included, more nucleic acid is encapsulated by liposome, smaller nucleic acid delivery carriers can be obtained, thereby improving the efficiency of transfection of nucleic acid, which is preferable.

4. Nucleic Acid Delivery Carrier

The nucleic acid delivery carrier of the embodiment comprises a complex and a nucleic acid delivery membrane.

The complex contains the nucleic acid condensing peptide describe above and nucleic acid. An example of the complex comprises the nucleic acid condensing peptide described above and nucleic acid. Or the complex includes the nucleic acid condensing peptide set described above and nucleic acid. An example of the complex comprises the nucleic acid condensing peptide set described above and nucleic acid. The nucleic acid may be, for example, the above-described nucleic acid. The nucleic acid may be contained in a complex while being condensed with a nucleic acid condensing peptide or a nucleic acid condensing peptide set. The complex may contain a plurality of kinds of nucleic acids.

The complex contains the nucleic acid condensing peptide of the embodiment and therefore it may contain a number of nucleic acids. When the complex includes a nucleic acid condensing peptide set and the nucleic acid condensing peptide set contains the second nucleic acid condensing peptide, the complex contains more nucleic acids.

The nucleic acid delivery membrane should preferably be a lipid composition. The lipid composition may be, for example, a composition in which lipids aggregate by noncovalent bond and its hydrophilic portion face an outer side to make a double layer. The lipids may just be, for example, a phospholipid derivative, a sphingolipid derivative, a cationic lipid, sterol, or any of these that is modified polyethylene glycol or the like, or any combination of these. The nucleic acid delivery membrane may be, for example, a conventionally known biomembrane.

The nucleic acid delivery membrane may be, for example, substantially spherical shape.

The nucleic acid delivery membrane may be, for example, liposome, vesicle or a capsule.

The nucleic acid delivery carrier of the embodiment is such that the complex is encapsulated in the nucleic acid delivery membrane. The number of complexes contained in the nucleic acid delivery membrane is not limited, but one to two is preferable. The particle diameter of the nucleic acid delivery carrier is not limited, but it may be, for example, 100 nm to 400 nm.

A large quantity of nucleic acid is encapsulated in the nucleic acid delivery carrier and the particle diameter of the nucleic acid delivery carrier is small. Therefore, when this nucleic acid delivery carrier is used, an even more quantity of nucleic acid can be transfected into a cell. In the case where the nucleic acid delivery carrier includes a nucleic acid condensing peptide set and the nucleic acid condensing peptide set contains the second nucleic acid condensing peptide, the nucleic acid delivery carrier contains more nucleic acid. Further, in this case, there is less nucleic acid which is not encapsulated in the nucleic acid delivery carrier as described above, nucleic acid delivery carriers cannot easily aggregate with each other, thereby making it possible to obtain a nucleic acid delivery carrier which can be more easily taken into a cell. When the third nucleic acid condensing peptide is included, the nucleic acid delivery carrier has even a smaller particle diameter.

The nucleic acid delivery carrier described above can be used for, for example, cell detection, functional modification of a cell, extinction of a cell, substance production in a cell, or the like, but the use is not limited to these.

Here, the cell detection is defined as to detect the characteristics of a cell, for example, whether or not a cell is in a state that a specific gene may be expressed in the cell, or detect as to whether a cell is normal, abnormal or the like, by transfecting a nucleic acid into the cell using the nucleic acid delivery carrier comprising a nucleic acid containing the above-described reporter gene expression cassette and detecting the signal from the reporter gene. An abnormal cell may be a cell affected by a specific disease. Examples of the specific disease may be cancer, psychiatric disorder, lifestyle-related disease, neurological diseases, autoimmune disease, cardiovascular disease and the like, or may be a presymptomatic disease, for example, a precancerous state, a prediabetic state or the like. By using the nucleic acid delivery carrier for cell detection, nucleic acid can be transfected into a cell more efficiently, and therefore detection of even higher sensitivity can be carried out.

Here, the functional modification of a cell is defined as, for example, addition of new cell function, compensation for weakened or lost normal cell function, suppression of a harmful effect in cell, differentiation of a cell or the like, which is carried out by transfecting nucleic acid into a cell using a nucleic acid delivery carrier comprising a nucleic acid which contains the above-described gene for modifying the function of the cell. By using a nucleic acid delivery carrier for functional modification of a cell, the function of the cell can be modified more efficiently. The functional modification of a cell may be carried out, for example, in the field of gene therapy or regenerative medicine or the like. By using this nucleic acid delivery carrier for gene therapy, the effect of treatment is improved. By using this nucleic acid delivery carrier for regenerative medicine, the cell which can differentiate or differentiated so as to a desired function can be obtained more efficiently.

Here, extinction of a cell is defined as, for example, to kill the cell by transfecting nucleic acid into the cell using a nucleic acid delivery carrier comprising the nucleic acid which contains the above-described gene which can lead the cell to apoptosis. The extinction of cells may be selective extinction of cells, for example, may be killing only the cells having specific characteristics among the cells to which the nucleic acid is transfected using the nucleic acid delivery carriers. Or, the cells may be killed by transfecting the gene which can lead the cells to apoptosis into the cell by a nucleic acid delivery carrier and prescribing drugs which can kill the cells specifically by existence of the gene. By using this nucleic acid delivery carrier for killing a cell, the cell can be killed more efficiently. The extinction of a cell is carried out, for example, in the field of gene therapy or the like. When this nucleic acid delivery carrier is used for gene therapy, the effect of the treatment improves more.

Here, the substance production in a cell is, for example, to make the cell produce a desired substance by transfecting nucleic acid into the cell using a nucleic acid delivery carrier comprising the nucleic acid which contains the above-described gene for the cell to produce the desired substance. When the substance production in a cell is carried out, more nucleic acid is transfected into the cell, and therefore the substance production in a cell can be carried out more efficiently.

When the nucleic acid delivery carrier including a nucleic acid condensing peptide set is used, the effect in each of the above-described usages can be further improved.

The nucleic acid delivery carrier may contain a desired function improving agent according to the above-listed usage. When used for cell detection, the function improving agent is, for example, a reagent for detecting a signal from a reporter gene. The reagent contains, for example, a substrate of reporter protein, an excipient, a stabilizer, a diluent or an adjuvant, or a combination of these. When used for functional modification of a cell, the function improving agent contains, for example, a drug for preventing, treating or dealing with the disease caused by the target cell, such as an anticancer agent, low molecule or antibody, a drug for promoting differentiation, or a combination of these. When used for extinction of a cell, the function improving agent contains, for example, actinomycin-D, cisplatin, bendamustine hydrochloride or betulic acid, or a combination of these. When used for substance production in a cell, the function improving agent contains, for example, a transcription accelerator and the like. When the nucleic acid delivery carrier is used for a usage other than those listed above, the function improving agent may also contain a desired drug used in that usage. These function improving agents may be encapsulated in the nucleic acid delivery membrane together with a complex.

The nucleic acid delivery carrier can be produced by a known method used, for example to encapsulate a small molecule into a biomembrane or the like. Such a method can be established by, for example, preparing a nucleic acid condensing peptide or a nucleic acid condensing peptide set; bringing the prepared nucleic acid condensing peptide or the nucleic acid condensing peptide set and the nucleic acid into contact with each other to obtain a complex; and encapsulating the complex into a nucleic acid delivery membrane to obtain a nucleic acid delivery carrier. The processing steps will now be described in detail.

First, a nucleic acid condensing peptide or a nucleic acid condensing peptide set is prepared. The nucleic acid condensing peptide or a nucleic acid condensing peptide set can be produced by any known method. For example, nucleic acid condensing peptides may be synthesized by a synthetic organic chemistry method or a gene engineering method. The nucleic acid condensing peptides may be dissolved in a solvent, for example. The solvent may be, for example, a buffer solution such as a HEPES buffer solution, a citrate buffer solution, a Tris buffer or a phosphate buffer, or physiological saline or water. When preparing a nucleic acid condensing peptide set containing the third nucleic acid condensing peptide, the third nucleic acid condensing peptide may be reserved in a separate solution from that of the other nucleic acid condensing peptide.

Next, the nucleic acid condensing peptide or the nucleic acid condensing peptide set, and the nucleic acid are brought into contact with each other to obtain a complex. The nucleic acid may be dissolved in a solvent before being brought into contact with the nucleic acid condensing peptide. Such a solvent may be, for example, a buffer solution such as a HEPES buffer solution, a citrate buffer solution, a Tris buffer or a phosphate buffer, or a physiological saline or water. In that case, the concentration of the nucleic acid to the entire solution should preferably be 0.1 mg/ml to 2.0 mg/ml, although which is not particularly limited.

Bringing the nucleic acid condensing peptide or the nucleic acid condensing peptide set, and the nucleic acid into contact with each other may be carried out, for example, by adding the nucleic acid to any of the above-listed solvents which contains the nucleic acid condensing peptide or the nucleic acid condensing peptide set, or adding the nucleic acid condensing peptide to a solvent containing the nucleic acid. The addition should preferably be carried out while stirring. Here, the weight ratio of the nucleic acid condensing peptide to the nucleic acid in the final solution should preferably be 0.7 to 1. When the nucleic acid condensing peptide set in which the third nucleic acid condensing peptide is reserved in another solvent is used, it is preferable that the third nucleic acid condensing peptide may be added after bringing the other nucleic acid condensing peptides and the nucleic acid into contact each other to condense the nucleic acid, thereby bringing the nucleic acid aggregate and the third nucleic acid condensing peptide into contact with each other. The bringing into contact should be carried out while stirring. With the bringing into contact, the complex may be obtained.

Subsequently, the complex is encapsulated with the nucleic acid delivery membrane. The nucleic acid delivery membrane may be one described above. The encapsulation may be carried out by the known method used, for example, for encapsulating a small molecule in a biomembrane or the like. Such a method may include, for example, addition of the obtained complex to a lipid solution which contains the above-described lipid, which is the material of the nucleic acid delivery membrane. The lipid solution may contain, for example, ethanol, chloroform, methanol or the like as a solvent in addition to the lipid. Although it is not particularly limited, the lipid solution should preferably contain the lipid at a concentration of 1.0 mg/ml to 1.5 mg/ml, for example. The addition should preferably be carried out while stirring.

With the addition, the complex may be encapsulated in the nucleic acid delivery membrane. Thus, a nucleic acid delivery carrier can be obtained.

The obtained nucleic acid delivery carrier may be dissolved into the solvent. The solvent may be, for example, a buffer solution such as HEPES, a citrate buffer solution, a Tris buffer or a phosphate buffer, or physiological saline or water.

5. Nucleic Acid Delivery Method

According to an embodiment, a nucleic acid delivery method using the above-described nucleic acid condensing peptide is provided.

Figure 2:
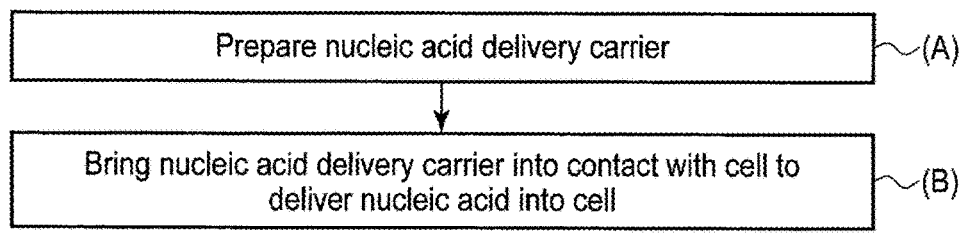
FIG. 2 is a flowchart showing an example of a nucleic acid delivery method of an embodiment.

FIG. 2 shows an example of the nucleic acid delivery method of the embodiment. The nucleic acid delivery method includes: (A) preparing a nucleic acid delivery carrier; and (B) bringing the nucleic acid delivery carrier into contact with a cell and delivering the nucleic acid to the cell.

Step (A) can be carried out by producing any desired one of the nucleic acid delivery carriers described above by any of the methods described above.

In step (B), the nucleic acid delivery carrier obtained in step (A) is brought into contact with a cell and the nucleic acid is delivered into the cell.

The cell may be of, for example, a human, an animal or vegetable origin. The cell may be a cell in the living body, or a cell which has been taken out of the organism. The cell may be one contained in a sample, for example, a biomaterial such as blood, hemocyte, urine, feces, sweat, saliva, oral mucosa, expectoration, lymph, spinal fluid, lacrimal fluid, mother milk, amniotic fluid, semen, tissue, biopsy or culture cell, or a material formulated by using any of these as materials. The cell may be, for example, one isolated or one established as cell strain.

The nucleic acid delivery carrier is brought into contact with such a cell. If the cell is one which has been taken out of an organism, the bringing into contact may include, for example, suspension of the cell in a culture medium, a buffer solution, physiological saline or the like and addition of the nucleic acid delivery carrier to the suspension. Or it may also include addition of the nucleic acid delivery carrier directly into a sample containing the cell. After adding the nucleic acid delivery carrier, it is preferable to stirring the mixture gently. Further, after adding the nucleic acid delivery carrier, the cell may be cultured. The culture may be carried out for about 4 hours to about 12 hours or even more, for example, under temperature conditions and carbon dioxide conditions, suitable for the culture of the cell.

When the cell is one in the living body, the bringing into contact is carried out by, for example, administering the nucleic acid delivery carrier to the organism which contains the target cell to be brought into contact with the carrier. The administration can be carried out via, for example, a parenteral way such as injection or intravenous drip into a subcutaneous site, a vein, muscles, a joint, a synovial membrane, a sternum, a pulp cavity, an eye, a liver, a lesion and an intracranial site.

With the bringing into contact, the nucleic acid delivery carrier is transfected into the cell and the nucleic acid can be delivered to the cell. The nucleic acid may be transfected into the nucleus.

In a further embodiment, the nucleic acid delivery method may also include a step of opening a pore in the cell membrane of a cell before or after bringing the nucleic acid delivery carrier into contact with the cell. The step of opening the pore in a cell membrane may be carried out by, for example, an electric perforation or an ultrasonic perforation. It may be carried out by, for example, applying voltage or ultrasonic waves to the cell.

According to the nucleic acid delivery method, it is possible to deliver a great quantity of nucleic acid efficiently to a cell. Moreover, the nucleic acid transfected into the cell is dissociates efficiently with the nucleic acid condensing peptide, and is expressed efficiently.

The nucleic acid delivery method can be used to transfect nucleic acid into a cell, for example, in the cell detection, the functional modification of a cell, the extinction of a cell, the substance production in a cell and the like, which are not particularly limited to these. When this method is used, cell detection with higher sensitivity, functional modification and extinction of a cell with higher efficiency, gene therapy with a higher effect, and substance production by a cell with higher efficiency can be achieved in each usage as described above.

6. Cell Production Method

According to an embodiment, a method of producing a cell using the above-described nucleic acid condensing peptide is provided.

The method of producing a cell comprises: (C) preparing a nucleic acid delivery carrier; (D) bringing the nucleic acid delivery carrier into contact with a cell, thereby delivering the nucleic acid into the cell; (E) culturing the cell obtained in the step (D); and (F) selecting a cell into which nucleic acid is transfected among the cultured cells.

The steps (C) and (D) can be carried out by executing the nucleic acid delivery method described in connection with the above-described steps (A) and (B).

In the step (E), the cell obtained in step (D) is cultured. The culture can be carried out by, for example, a known culture method suitable for culturing the cell used here. Although not particularly limited, the culture may be carried out by, for example, incubating the cell on an appropriate culture medium for about 4 to 12 hours or more under suitable conditions of carbon dioxide concentration and temperature.

In the step (F), the cells into which the nucleic acid is transfected are selected. Although not particularly limited, when a drug resistance gene expression cassette is included in the nucleic acid to be contained in the nucleic acid delivery carrier, the selection is carried out by, for example, treating the cells with the corresponding drug. Or, for example, when a reporter gene expression cassette is included in the nucleic acid, signal detection from the reporter gene is carried out and the cells detected to exhibit a desired signal can be extracted, left or recorded as the selection.

According to the cell production method, it is possible to obtain, with higher efficiency, the cell which includes more nucleic acid to be transfected and to be expressed efficiently. Further, although not particularly limited, according to the nucleic acid production methods, for example, the cell whose new function, the cell whose normal function has been once weakened or lost and more sufficiently compensated, the cell whose harmful effect has been more suppressed, and the cell which can be or have been differentiated into cells having a desired function can be produced more efficiently. Therefore, more effective treatment can be carried out in gene therapy, regenerative medicine and the like. Further, the cell which produces a larger quantity of substance can be produced.

7. Cell Detection Method

According to an embodiment, a cell detection method using a nucleic acid delivery technique is provided.

Figure 3:
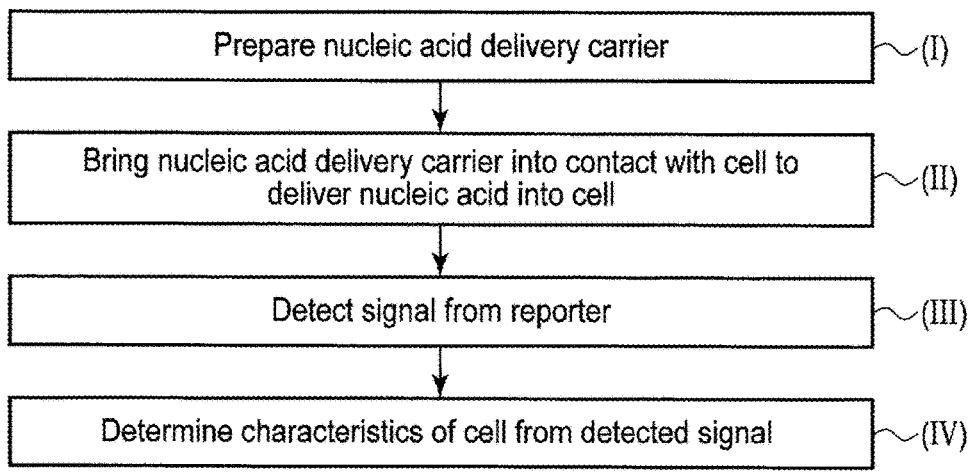
FIG. 3 is a flowchart showing an example of a cell detection method of an embodiment.

FIG. 3 shows an example of the cell detection method of the embodiment. The cell detection method comprises: (I) preparing a nucleic acid delivery carrier; (II) bringing the nucleic acid delivery carrier into contact with a cell to deliver nucleic acid into the cell; (III) detecting a signal from a reporter gene contained in the nucleic acid; and (IV) determining the characteristics of the cell based on the detected signal. Here, the nucleic acid contained in the nucleic acid delivery carrier contains a reporter gene expression cassette containing a reporter gene.

Steps (I) and (II) can be carried out by executing the nucleic acid delivery method described in connection with the above-described steps (A) and (B) with use of a nucleic acid delivery carrier comprising a nucleic acid containing a reporter gene expression cassette which contains a reporter gene.

In step (III), the signal from the reporter gene is detected. The signal from the reporter gene may be, for example, a signal from the reporter protein produced by the expression of the reporter gene. The detection of a signal may be detection of the presence or absence of a signal or detection of the intensity of a signal. For the detection of a signal, a known device selected according to the type of the reporter protein and/or the type of the signal may be used. Examples of the device may include a luminometer, a fluorometer, an X-ray measuring device, an electron spin resonating device, a nuclear medicine diagnostic device, a magnetic resonance imaging device and/or a luminescence/fluorescent microscope, etc.

If needed, a reagent for detecting the signal may be used as a function improving agent. The reagent may be, for example, a substrate of a reporter protein, an excipient, a stabilizer, a diluent and/or an adjuvant, etc. The reagent may be encapsulated in the nucleic acid delivery carrier or may be added later.

In step (IV), the characteristics of the cell are determined based on the signal detected in the step (III) described above.

The reporter gene is a gene which changes whether the existence or non-existence of expression or varies the quantity of expression with the characteristics of the cell, and therefore it can determine the characteristics of the cell with the existence or non-existence of expression or the quantity of expression of the reporter gene.

The determination of the characteristics of a cell may be determining whether or not a specific nucleic acid is transfected into the cell, whether the cell is normal or abnormal based on the existence/non-existence or strength of the signal detected in step (III). Further, it may be determining where the cell is abnormal and simultaneously or thereafter, determining the kind of disease which the cell is affected. Examples of the specific disease may be those listed above.

If needed, separately, the characteristics of a cell may be determined by comparing the detection result obtained in step (III) and the amount of detection of the reporter protein acquired from an object cell whose characteristics are known, with each other.

The determination of cell characteristics may be carried out by, for example, using the value obtained by a known device which automatically evaluates the detected signal or by observing the cell using the luminescence/fluorescence microscope or the like.

According to the method, nucleic acid is transfected into a cell efficiently and expressed efficiently, the characteristics of the cell can be determined with high precision. Thus, for example, abnormal cells can be detected with high sensitivity.

8. Kit

According to a further embodiment, a kit containing a nucleic acid delivery carrier is provided.

The kit contains any one of the above-described nucleic acid delivery carriers, and desirably a function improving agent.

The nucleic acid delivery carrier may be sealed in a container with a solvent to be included in an assay kit. The solvent may be, for example, a buffer solution such as HEPES buffer solution, citrate buffer solution, Tris buffer or phosphate buffer, or a physiological saline or water. The kit may include a plurality of kinds of nucleic acid delivery carriers.

The function improving agent is any of the above-described function improving agents. The kit may contain a plurality of kinds of function improving agents.

The nucleic acid delivery carriers and the function improving agents may be contained in a container individually or in any combination thereof.

The kit may be a kit for detecting nucleic acid. In that case, the nucleic acid contained in the nucleic acid delivery carrier contains a reporter gene expression cassette, and the function improving agent contains the reagent for detecting a signal from the reporter gene contained in a nucleic acid. The reagent may be, for example, a substrate of a reporter protein, an excipient, a stabilizer, a diluent and/or an adjuvant, or a combination of any of these.

When the kit is used, nucleic acid is efficiently transfected into a cell and expressed efficiently, and therefore the characteristics of the cell can be determined with high precision. Thus, for example, cells can be detected with high sensitivity.

The kit may be a kit for modifying the function of a cell. In that case, the nucleic acid contained in the nucleic acid delivery carrier contains a gene expression cassette which includes a gene for modifying the function of the cell, that is, for example, a gene for adding new cell function, a gene for compensating for the normal function which has been once weakened or lost, a gene for suppressing a harmful effect in cell, a gene for differentiating a cell or the like, and the function improving agent contains a drug for preventing, treating or dealing with a disease caused by the target cell, that is, for example, an anticancer agent, low molecule or antibody, a drug for promoting differentiation, or a combination of these.

When this kit is used, the function of a cell can be modified more efficiently.

The kit may be a kit for killing a cell. In that case, the nucleic acid contained in the nucleic acid delivery carrier contains a gene expression cassette containing a gene which leads the cell to apoptosis, and the function improving agent contains actinomycin-D, cisplatin, bendamustine hydrochloride or betulic acid, or a combination of these. When this kit is used, the cells can be killed more efficiently.

The kit may be a kit for producing a substance in a cell. In that case, the nucleic acid contained in the nucleic acid delivery carrier contains a gene expression cassette which contains a gene for the cell to produce a desired substance, and the function improving agent contains a transcription promoter or the like. When this kit is used, more nucleic acid can be transfected into a cell, and therefore the substance can be produced in the cell more efficiently.

When the kit containing the nucleic acid delivery carrier which contains the nucleic acid condensing peptide set is used, the effect obtained in each of the above-described usage can be further improved.

EXAMPLES

Example 1

The condensability of the nucleic acid by the peptide of the embodiment and the potential of the peptide-nucleic-acid complex were evaluated.

Five kinds of peptides shown in Table 1, namely, a protamine-originated peptide sequence of salmon origin (which will be referred to as "protamine" hereinafter), mHP-1, mHP-2, mHP-3 and mHP-4 were produced.

TABLE 1

|  | Sequences | SEQ ID NO. | Number of residual amino acids |
|---|---|---|---|
| mHP-1 | RQRQRYYRQRQRGGRRRRRR | 1 | 20 |
| mHP-2 | RRRRRRYYRQRQRGGRRRRRR | 3 | 21 |
| mHP-3 | RQRQRGGRRRRRR | 2 | 13 |
| mHP-4 | RRRRRRGGRRRRRR | 4 | 14 |
| Protamine sequence | PRRRRSSSRPIRRRRPRRASRRRRRRGGRRRR | 5 | 32 |

The peptides were each dissolved in 10 mM of HEPES (pH: 5.3) to prepare several peptide solutions having different peptide concentrations.

For the protamine, three peptide solutions were prepared to have peptide concentrations of: (1) 2.1 mg/ml, (2) 2.4 mg/ml and (3) 2.7 mg/ml. For the mHP-4, four peptide solutions were prepared to have peptide concentrations of: (4) 1.8 mg/ml, (5) 2.1 mg/ml, (6) 2.4 mg/ml and (7) 2.7 mg/ml. For the mHP-1, three peptide solutions were prepared to have peptide concentrations of: (8) 2.1 mg/ml, (9) 2.4 mg/ml and (10) 2.7 mg/ml. For the mHP-2, five peptide solutions were prepared to have peptide concentrations of: (11) 1.2 mg/ml, (12) 1.5 mg/ml, (13) 2.1 mg/ml, (14) 2.4 mg/ml and (15) 2.7 mg/ml. For the mHP-3, three peptide solutions were prepared to have peptide concentrations of: (16) 2.1 mg/ml, (17) 2.4 mg/ml and (18) 2.7 mg/ml. Further, plasmid vector (pDNA) was diluted with purified water to prepare a nucleic acid solution having a pDNA concentration of 3.0 mg/ml.

18 sets of nucleic acid solutions (90 μL) put in tubes were prepared and the peptide solutions (1) to (18) (90 μL) described above were dropped respectively therein and mixed while stirring each, to condense the nucleic acids. Thus, the peptide-nucleic-acid complexes were obtained. Then, the mixtures were each diluted with purified water to 25-fold to produce peptide-nucleic-acid solutions. Further, as references, samples containing only each respective peptide were also prepared without adding the nucleic acid solutions thereto.

The average particle diameter and Zeta potential of each of the peptide-nucleic-acid complexes were investigated using the peptide-nucleic-acid solutions. The average particle diameter and Zeta potential were measured using a zetasizer.

Figure 4:
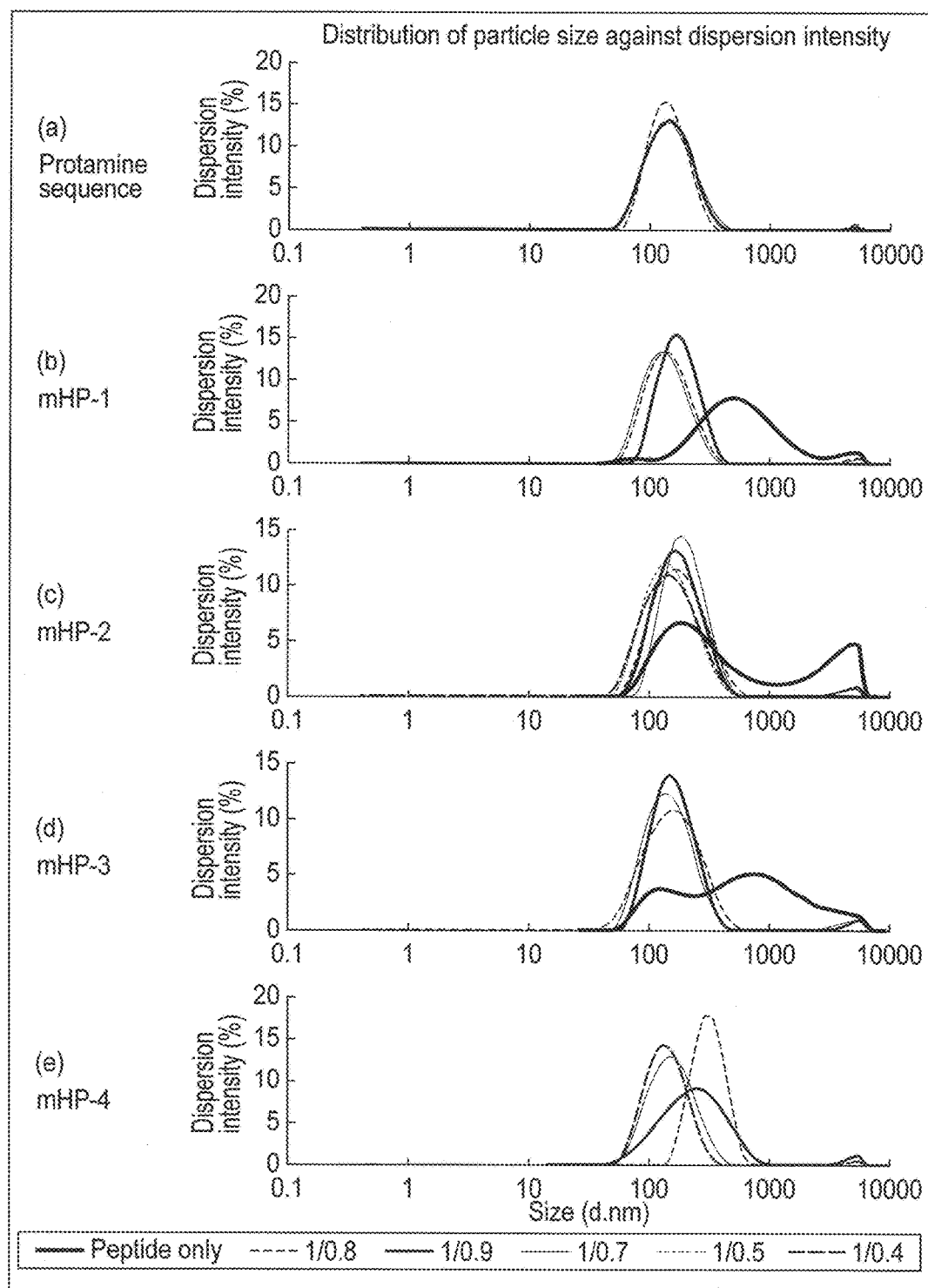
FIG. 4 is a graph showing test results of Example 1.
Figure 5:
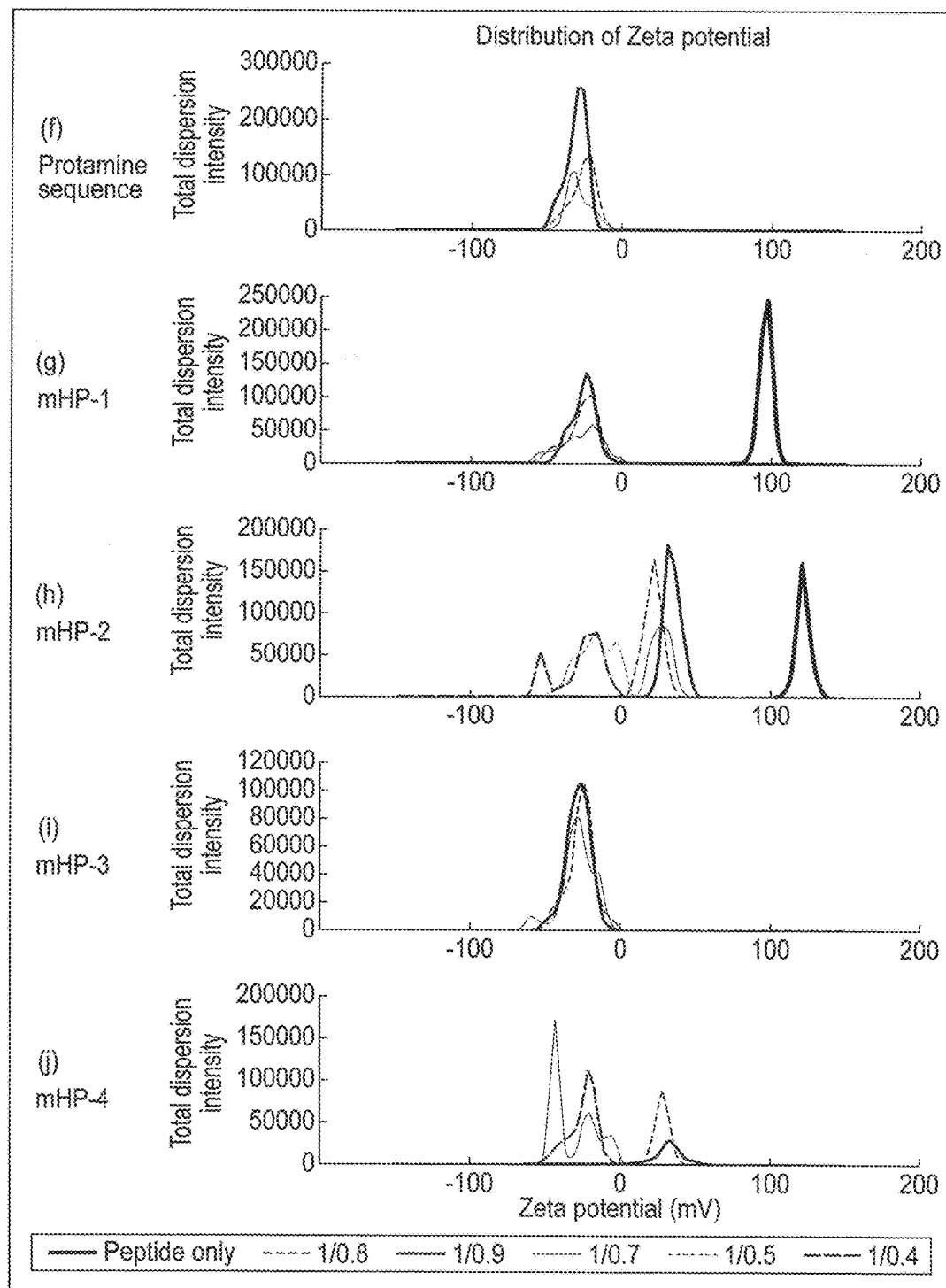
FIG. 5 is a graph showing test results of Example 1.

The results are shown in Table 2 and FIGS. 4 and 5. Items (a) to (e) of FIG. 4 each show distribution of the particle diameter of the peptide-nucleic-acid complex contained in the respective peptide-nucleic-acid solution. Items (f) to (j) of FIG. 5 each show distribution of the Zeta potential of the peptide-nucleic-acid complex contained in the respective peptide-nucleic-acid solution.

TABLE 2

| No. | Peptides | Mixture ratio (pDNA/peptide (peptide conc.)) | Average particle diameter (zAve · nm) | Zeta potential (mV) |
|---|---|---|---|---|
| Reference | Protamine sequence | Protamine sequence solely | 711.3 | 28.1 |
| 1 |  | 1/0.7 (2.1 mg/mL) | 136.5 | −27.8 |
| 2 |  | 1/0.8 (2.4 mg/mL) | 135.9 | −24.9 |
| 3 |  | 1/0.9 (2.7 mg/mL) | 139.6 | −29.5 |
| Reference | mHP-4 | mHP-4 solely | 1083.0 | 39.7 |
| 4 |  | 1/0.6 (1.8 mg/mL) | 130.9 | −23.8 |
| 5 |  | 1/0.7 (2.1 mg/mL) | 141.2 | −30.7 |
| 6 |  | 1/0.8 (2.4 mg/mL) | 323.4 | 28.6 |
| 7 |  | 1/0.9 (2.7 mg/mL) | 212.2 | 33.0 |
| Reference | mHP-1 | mHP-1 solely | 444.0 | 37.2 |
| 8 |  | 1/0.7 (2.1 mg/mL) | 124.0 | −28.2 |
| 9 |  | 1/0.8 (2.4 mg/mL) | 133.4 | −26.7 |
| 10 |  | 1/0.9 (2.7 mg/mL) | 158.0 | −25.5 |
| Reference | mHP-2 | mHP-2 solely | 321.0 | 50.5 |
| 11 |  | 1/0.4 (1.2 mg/mL) | 141.8 | −27.7 |
| 12 |  | 1/0.5 (1.5 mg/mL) | 139.8 | −17.7 |
| 13 |  | 1/0.7 (2.1 mg/mL) | 184.0 | 27.3 |
| 14 |  | 1/0.8 (2.4 mg/mL) | 159.0 | 21.6 |
| 15 |  | 1/0.9 (2.7 mg/mL) | 158.6 | 34.2 |
| Reference | mHP-3 | mHP-3 solely | 322.9 | 17.0 |
| 16 |  | 1/0.7 (2.1 mg/mL) | 135.8 | −28.1 |
| 17 |  | 1/0.8 (2.4 mg/mL) | 134.9 | −25.9 |
| 18 |  | 1/0.9 (2.7 mg/mL) | 148.2 | −28.3 |

From the results of Table 2, FIGS. 4 and 5, it has been clarified that the samples using mHP-1 and mHP-3 each have a smaller average particle diameter and a smaller dispersion in diameter as compared to those of the other samples. From these results, the mHP-1 and mHP-3 are excellent in the characteristics of condensing the nucleic acid, and therefore peptide-nucleic-acid complexes of a uniform particle diameter can be formed. Thus, it has been suggested that a peptide comprising a peptide sequence whose one terminal is RQRQR and another terminal is RRRRRR exhibits an excellent nucleic acid condensing performance. Moreover, also in each sample, the value of Zeta potential is around −30 mV, and it has been clarified that a complex having such a charge which makes it easy to be encapsulated in liposome is formed.

Example 2

The condensability of the nucleic acid by the peptide of the embodiment and the dissociation of the peptide and the nucleic acid were estimated by a gel retardation assay.

As samples for the condensability evaluation, 18 sets of 8.0 μL of 10 mM-HEPES (pH: 5.3) were prepared and 1.0 μL of the respective peptide-nucleic-acid solutions of Example 1 and 1.0 μL of polyglutamic acid (PGA) solutions were added thereto and mixed, thus preparing mixtures. As samples for the dissociation evaluation, 1.0 μL of peptide-nucleic-acid solutions and 1.0 μL of poly-glutamic-acid (PGA) solutions were added to 8.0 μL of 10 mM-HEPES solutions (pH: 5.3) and mixed, thereby preparing mixtures. After they were let stand still for 15 minutes at room temperature, 1.0 μL of an electrophoretic buffer (50%-sucrose solution) was added to each mixture, and they were mixed well, to carry out electrophoresis with a 0.8%-agarose gel. After the electrophoresis, the nucleic acid dyed with ethidium bromide was visualized by UV irradiation, and the nucleic acids condensed by the peptide and the nucleic acid dissociating with the peptide and moving into a gel were detected.

Figure 6:
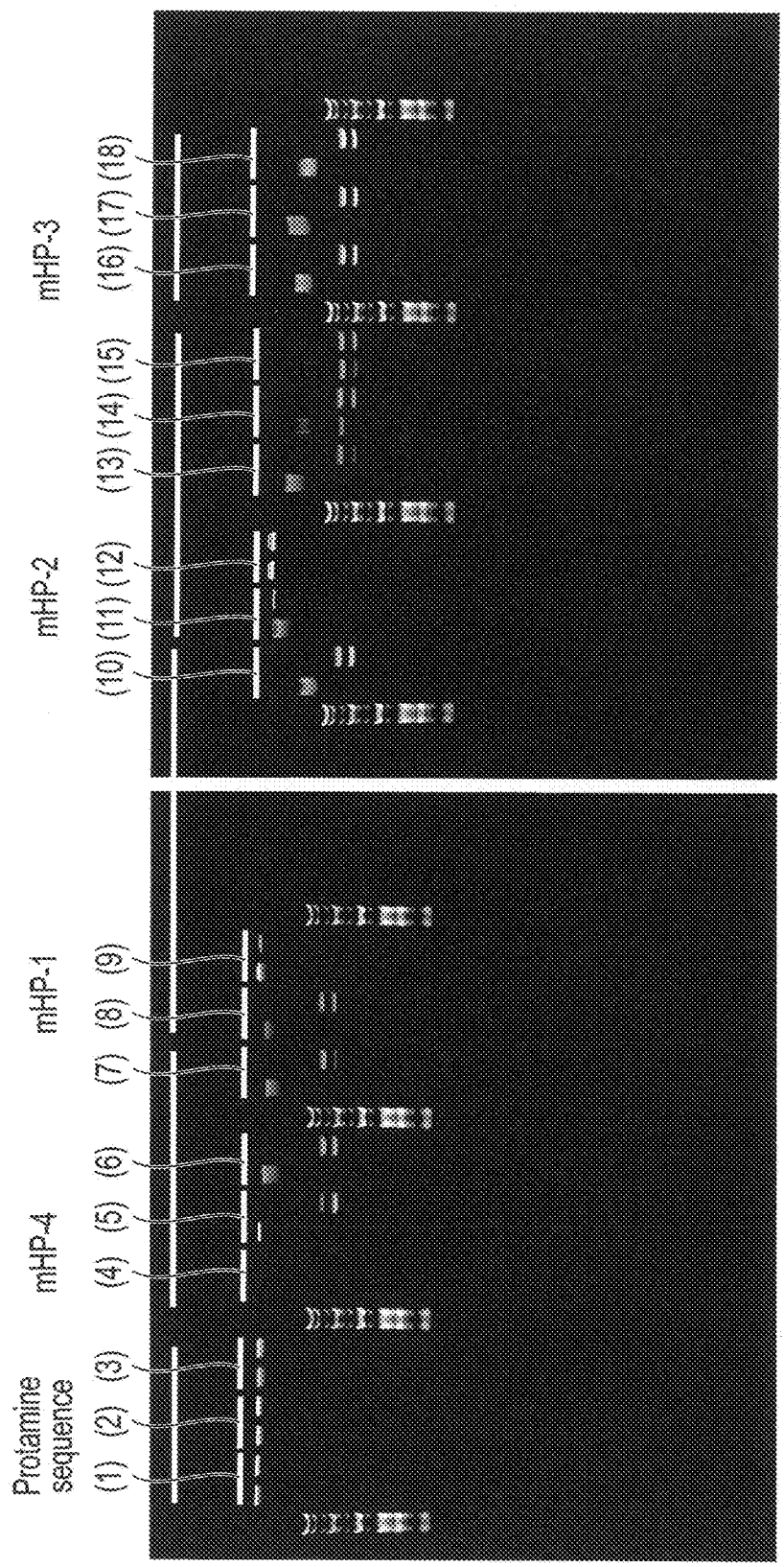
FIG. 6 is an electropherogram showing test results of Example 2.

FIG. 6 shows the results. FIG. 6 is a photograph showing the agarose gel subjected to UV irradiation. Of two lanes indicated by the numbers of the respective samples, the left lane indicates the results of a PGA (−) sample (sample for the condensability evaluation) and the right lane for those of a PGA (+) sample (sample for the dissociation evaluation).

When an integrated band with a large molecular weight, which strongly shines is observed in the left lane, it was evaluated as a high condensability. When two bands of a molecular weight of 5 to 7 kbp, which strongly shine were observed in the right lane, it was estimated as a high dissociation. The mHP-1 and mHP-3 were excellent both in condensability and dissociation in the samples of any concentration. In particular, they were excellent in the peptide-nucleic-acid solutions (8) and (16). Thus, it has been suggested that a peptide comprising a peptide sequence whose one terminal is RQRQR and another terminal is RRRRRR is more excellent in both nucleic acid condensing performance and dissociation than that whose both terminals are RRRRRR or a protamine-originated peptide sequence.

Example 3

The encapsulation of nucleic acid into liposome by the peptide of the embodiment was evaluated.

Encapsulation of Peptide and Nucleic Acid into Liposome

COATSOME/SS-20 (Nippon Oil & Fats), DOPE, cholesterol and DMG-PEG were dissolved into ethanol at a molar ratio of 5:3:1:0.3, to obtain a lipid solution. Two sets of lipid solutions (0.5 ml) put into tubes were prepared, and 0.5 ml of peptide-nucleic-acid solutions (8) (mHP-1) and (16) (mHP-3) of Example 1 were dropped thereto while stirring each lipid solution, thereby forming liposomes. 9 ml of 10 mM-HEPES (pH: 5.3) was added to each of the liposome solutions to make a total amount of 10 ml (each liposome solution will be referred to as "Complex" hereinafter). Further, on an assumption that the liposome is taken into an organism, and liposome solutions (which will be referred to as "HEPES replacement") in which ethanol, which is the solvent of Complex is substituted by HEPES were produced. The HEPES replacements were produced by condensing each solution of Complex to 1.5 ml with an ultrafiltration film for 300 kDa, adding 8.5 ml of 100 mM-HEPES (pH: 7.4) to each, performing ultrafiltration, thereafter substituting the solvent with 10 mM-HEPES (pH: 7.4), and finally condensing to 0.5 ml. Further, the HEPES replacements were filtered for sterilization with a filter with a pore diameter of 0.45 μm to prepare solutions (which will be referred to as "0.45 μm" hereinafter).

Confirmation of Encapsulation

The "peptide-nucleic-acid solution", "HEPES substituent" and "0.45 micrometer", each of which contain the protamine, mHP-1 or mHP-3 prepared as above were examined in terms of average particle diameter of liposome, Zeta potential and amount of encapsulation of plasmid. The average particle diameter and Zeta potential were measured using a zetasizer. The amount of encapsulation of plasmid was measured using a Quant-iT PicoGreen (registered trademark) dsDNA assay kit.

The results are shown in Table 3, FIGS. 7 and 8. Items (a) to (c) of FIG. 7 each indicate the respective peptide-nucleic-acid solution contained in each solution and distribution of the particle diameter of the liposome. Items (d) to (f) of FIG. 8 each indicate the respective peptide-nucleic-acid solution contained in each solution and distribution of the Zeta potential of the liposome.

TABLE 3

| Peptides | | Average particle diameter (zAve · nm) | Zeta potential (mV) | Plasmid inclusion amount (μg/mL) |
|---|---|---|---|---|
| Protamine sequence | Peptide-nucleic acid solution | 167.8 | −41.30 | |
| | HEPES substitution | 392.2 | −0.47 | 12.68 |
| | 0.45 μm | 235.5 | −0.72 | 7.97 |
| mHP-1 | Peptide-nucleic acid solution | 121.4 | −44.50 | |
| | HEPES substitution | 254.1 | −11.30 | 42.12 |
| | 0.45 μm | 222.0 | −5.26 | 37.30 |
| mHP-3 | Peptide-nucleic acid solution | 113.4 | −43.90 | |
| | HEPES substitution | 240.5 | −3.39 | 96.94 |
| | 0.45 μm | 218.2 | −2.95 | 84.14 |

Both samples of the mHP-1 and mHP-3 had a smaller average particle diameter and a more amount of encapsulation of plasmid as compared to those of the samples containing the protamine. Thus, it has been clarified that a peptide comprising a peptide sequence whose one terminal is RQRQR and another terminal is RRRRRR is more excellent in both nucleic acid condensing performance and encapsulation into liposome than that of a protamine-originated peptide sequence.

Example 4

The encapsulation of nucleic acid to liposome by the peptide of the embodiment was evaluated with a gel retardation assay.

As samples for the encapsulation evaluation, two sets of 8.0 μL of 10 mM-HEPES (pH: 7.0) were prepared and 1.0 μL of solutions of Complex respectively containing the mHP-1 or mHP-3 of Example 3 and sodium dodecyl sulfate (SDS, the final concentration: 1%) which cleavages liposome were added thereto, to prepare mixtures. In addition, as controls, a mixture to which 1.0 μL of a poly-glutamic-acid (PGA) solution was added in place of SDS, and a sample which contains neither SDS nor PGA were prepared. After the solutions were let stand still for 15 minutes at room temperature, 1.0 μL of an electrophoretic buffer (50%-sucrose solution) was added to each mixture, and they were mixed well, to carry out electrophoresis with a 0.8%-agarose gel. After the electrophoresis, the gel was immersed in an ethidium bromide solution to dye the nucleic acid and the gel was photographed while irradiating it with UV, thus detecting the nucleic acid.

Figure 9:
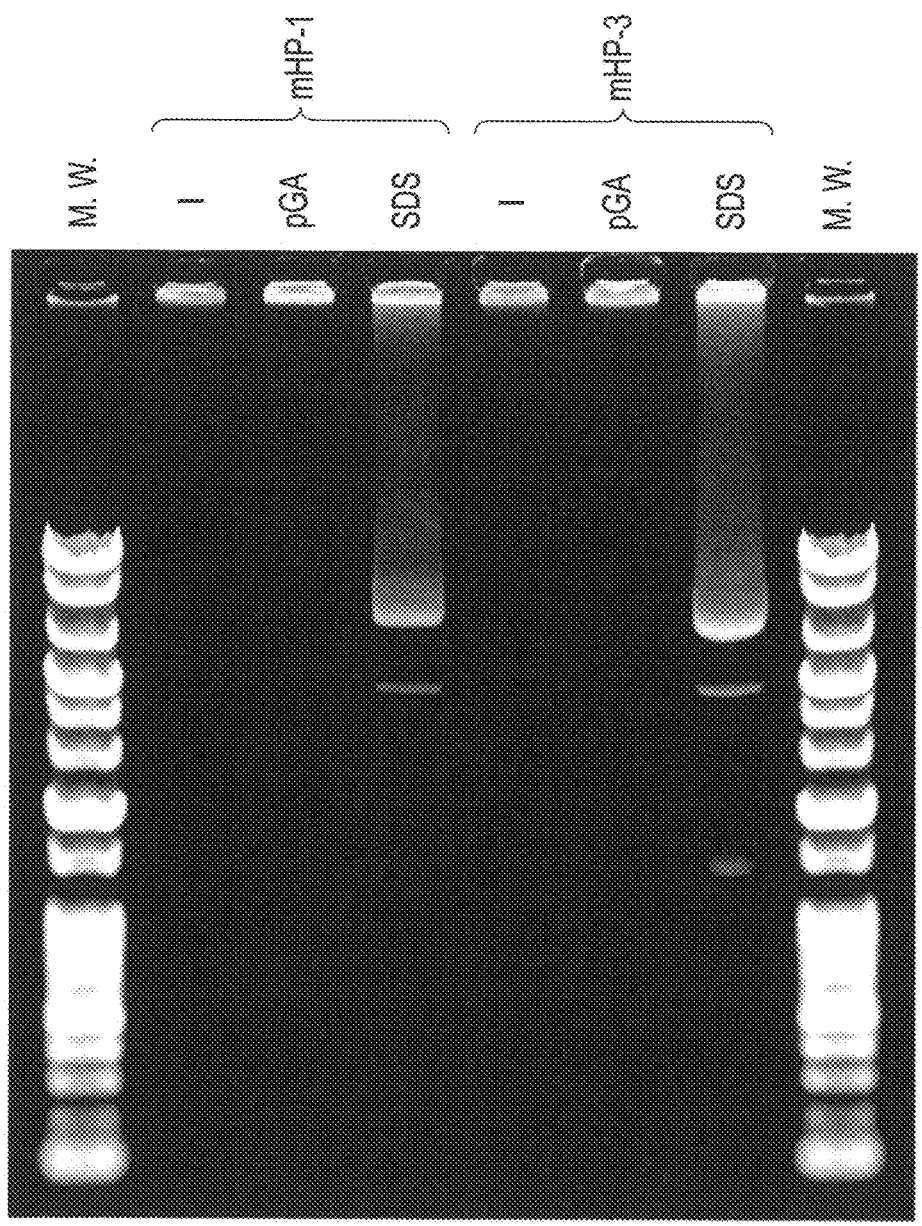
FIG. 9 is an electropherogram showing test results of Example 4.

The result was shown in FIG. 9. FIG. 9 is a photograph taken by irradiating the agarose gel with UV. In both samples of the mHP-1 and mHP-3, a band which shines strongly in a small molecular weight region was observed in the lane in which the solution containing SDS, in which the liposome was cleaved. From this result, it has been suggested that nucleic acid can be encapsulated well in the liposomes prepared using the peptides of mHP-1 and mHP-3.

Example 5

The transfection degree of nucleic acid to a cell by a liposome encapsulating nucleic acid by the peptide of the embodiment was evaluated.

Production of Liposome

As nucleic acid to be encapsulated in the liposome, pAmp-CMV-nLuc was used. The pAmp-CMV-nLuc is a reporter vector which contains a NanoLuc gene as the reporter gene. The pAmp-CMV-nLuc includes a CMV promoter as a gene expression promoter, and in its lower stream, a NanoLuc gene, IRES sequence and a replication initiation protein (LT, large T antigen) gene of simian virus 40 (SV40) which are liked in this order, and further, in a lower stream, a replication initiation sequence (SV40 ori) of SV40. Using this nucleic acid, the protamine of Example 3 and the peptides of the mHP-1 and mHP-3, a liposome solution was produced by a method similar to that of Example 3.

Transfection of Liposome into Cell

The liposome solution prepared as above was added to human normal mammary gland epithelial cells (HMEC) (Kurabo Industries). The HMEC used here was prepared by reviving from an HMEC freeze stock and thereafter culturing in an incubator of a 5%-$CO_2$ atmosphere at 37 degrees Celsius for six to seven days. The culture medium which cultured the HMEC was prepared by adding MammaryLife Life Factors (Kurabo Industries) to MammaryLife Basal Medium (Kurabo Industries) and the final concentrations of the ingredients in the culture medium were: 5 mg/ml of insulin, 6 mM of L-glutamine, 1 mM of epinephrine, 5 mg/ml of apotransferrin, 0.5 ng of TGFa, 0.4% of Extract P and 100 ng/mL of hydrocortisone succinate. After the culturing, the HMEC was peeled off from the bottom surface of the culture medium using 0.05% of trypsin EDTA and then collecting cells by centrifuge at 200×g for 3 minutes. After that, a fresh culture medium was used to adjust the number of cells was 1.4 to 1.6×$10^4$ cells/100 μL. To 150 μL of a suspension of the cells, 10 μL of the liposome solution was added and mixed gently, and then the cells were further cultured under a 5%-$CO_2$ atmosphere at 37° C.

Detection of Cell 48 hours after the addition of the liposome, a luminescence substrate (Nano-Glo Luciferase Assay Substrate and Promega) was added to the culture medium to dilute to 1/2000. This culture dish was set to LV200 (a luminescence imaging system of Olympus) and photographed. The shooting conditions were as follows: object-glass magnification: ×20, imaging lens magnification: ×0.2, exposure time: 100 ms for bright fields and 1 min and 5 min for dark fields, EMGain: 4 for bright fields and 610 for dark fields. The control of LV200 and ImageMEX and the image processing of the shot images of the bright fields and dark fields were carried out by MetaMorph (Molecular Device).

Figure 10:
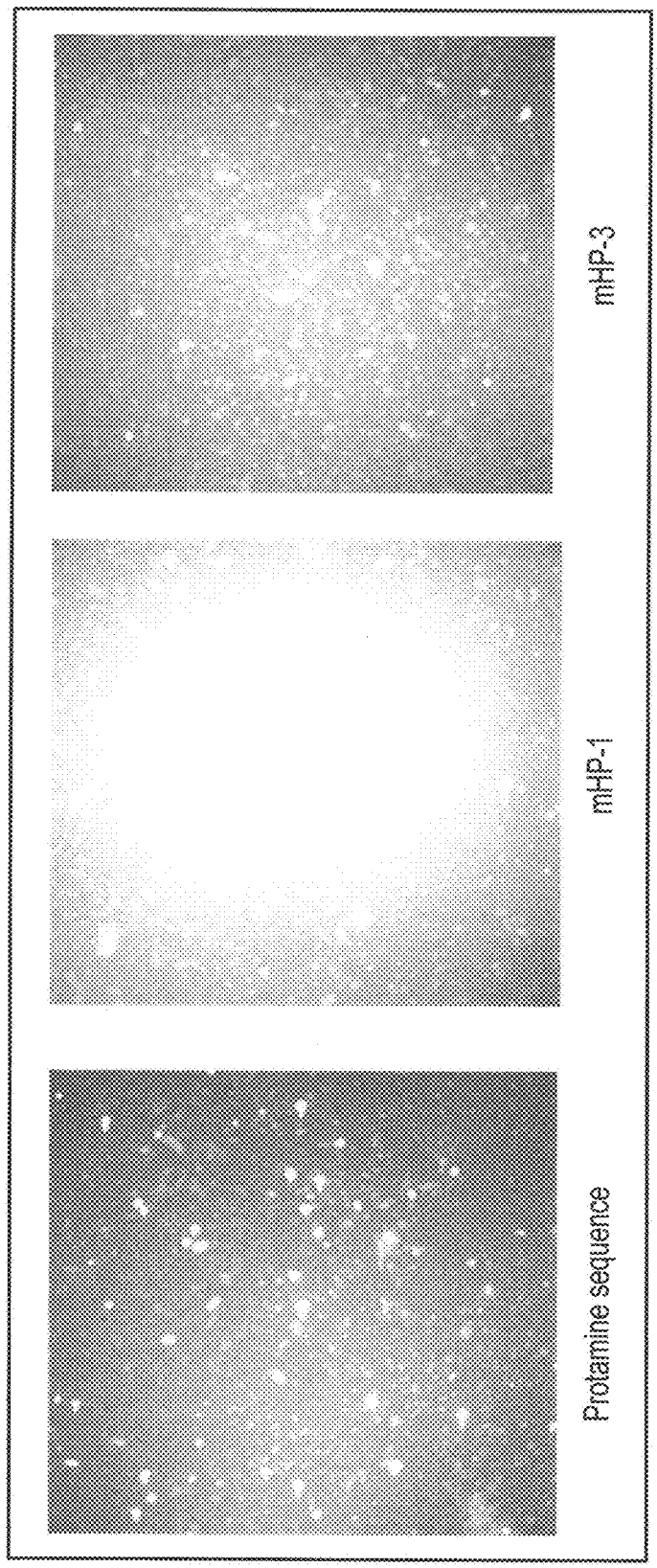
FIG. 10 is a photomicrograph showing test results of Example 5.

The results are shown in FIG. 10. The white luminescent points in the photographs are cells in which the vector was transfected and the reporter gene was expressed. In the sample using the mHP-1, luminescence was observed in most cells. In the sample using the mHP-3, luminescence was observed in more cells than those of the sample which used the protamine. From this result, it has been suggested that according to the method of delivering nucleic acid to a cell using mHP-1 and mHP-3, a more amount of nucleic acid delivery to a cell and a more amount of expression of the delivered nucleic acid are obtained. As a reason for this result, it can be considered that the mHP-1 and mHP-3 are superior in the nucleic acid condensing and dissociation as well as in the encapsulation of nucleic acid into liposome comparing to the protamine as indicated by the results of Examples 1 to 4.

From the above-provided test results, it has been clarified that the peptide of the embodiment is more excellent in nucleic acid condensing and nucleic acid dissociation than the conventional techniques. Further, as a result, nucleic acid is efficiently encapsulated by liposome with the peptide of the embodiment. With the method of delivering the nucleic acid of the embodiment using the liposome to a cell, more nucleic acids can be transfected into the cell with higher efficiency, and further the nucleic acids delivered to the cell by the method can be expressed more efficiently and the cells in which the nucleic acids were expressed can be detected.

Example 6

The condensability of the nucleic acid by the peptide of the embodiment and the potential of the peptide-nucleic-acid complex were evaluated.

Two kinds of peptides shown in Table 4, namely, mHP-1, and mHP-2 were produced.

TABLE 4

|  | Sequences | SEQ ID NO. | Number of residual amino acids |
|---|---|---|---|
| mHP-1 | RQRQRYYRQRQRGGRRRRRR | 1 | 20 |
| mHP-2 | RRRRRRYYRQRQRGGRRRRRR | 3 | 21 |

Each of the peptides was dissolved into 10 mM-HEPES (pH: 5.4) to prepare several peptide solutions having different peptide concentrations.

For the mHP-1, one peptide solution was prepared to have a peptide concentration of (1) 0.24 mg/ml. For the mHP-2, one peptide solution was prepared to have a peptide concentration of (2) 0.24 mg/ml. For the mHP-1 and mHP-2, five peptide solutions were prepared to have a total peptide concentration of 0.24 mg/ml and mixture ratios between mHP-1 and mHP-2 of: (3) 1:1, (4) 1:3, (5) 1:5, (6) 1:7 and (7) 1:9. Meanwhile, plasmid vector (pDNA) was diluted with purified water to prepare a nucleic acid solution having a pDNA concentration of 0.15 mg/ml.

The peptide solutions (1) to (7) (100 μL) were prepared in tubes and the nucleic acid solution (200 μL) was dropped and mixed thereto while stirring each solution to condense the nucleic acids, and thus peptide-nucleic-acid complexes were obtained.

The peptide-nucleic-acid complexes were investigated in terms of average particle diameter, polydispersity index and Zeta potential using the respective peptide-nucleic-acid solutions. The average particle diameter, polydispersity index and Zeta potential were measured using a zetasizer.

The results are shown in Table 5.

TABLE 5

| No. | Peptide mixture ratio (mHP-1:mHP-2) | Average particle diameter (zAve · nm) | Polydispersity index (PDI) | Zeta potential (mV) |
|---|---|---|---|---|
| 1 | 1:0 | 156.6 | 0.190 | −31.1 |
| 2 | 1:1 | 147.4 | 0.216 | −29.5 |
| 3 | 1:3 | 143.7 | 0.221 | −31.6 |
| 4 | 1:5 | 160.9 | 0.264 | −30.4 |
| 5 | 1:7 | 146.3 | 0.224 | −28.7 |
| 6 | 1:9 | 146.4 | 0.213 | −32.4 |
| 7 | 0:1 | 169.1 | 0.285 | −34.1 |

The results of Table 5 indicate that in any samples, the average particle diameter was around 140 to 160 nm, the PDI was 0.3 or less, and the Zeta potential value was around −30 mV. Thus, it has been found that regardless of the mixture ratio between mHP-1 and mHP-2, the peptide-nucleic-acid complexes having a particle diameter and a charge, easy to be encapsulated in liposome, were formed homogeneously.

Example 7

The condensability of the nucleic acid by the peptide of the embodiment and the dissociation of the peptide and nucleic acid were evaluated by a gel retardation assay.

As samples for the condensability evaluation, seven sets of 5.5 µL of 10 mM-HEPES (pH: 5.4) were prepared, and 4.5 µL of the respective peptide-nucleic-acid solutions of Example 6 were added to prepare mixtures. As samples for the dissociation evaluation, seven sets of 4.5 µL of 10 mM-HEPES (pH: 5.4) were prepared and 4.5 µL of the respective peptide-nucleic-acid solutions of Example 6 and 1.0 of a poly-glutamic-acid (PGA) solution were added thereto to prepare mixtures. After they were let stand still for 10 minutes at room temperature, 1.0 µL of an electrophoretic buffer (50%-sucrose solution) was added to each mixture, and they were mixed well, to carry out electrophoresis with a 0.8%-agarose gel. After the electrophoresis, the nucleic acid dyed with ethidium bromide was visualized by UV irradiation, and the nucleic acids condensed by the peptide and the nucleic acid dissociating with the peptide and moving into a gel were detected.

Figure 11:
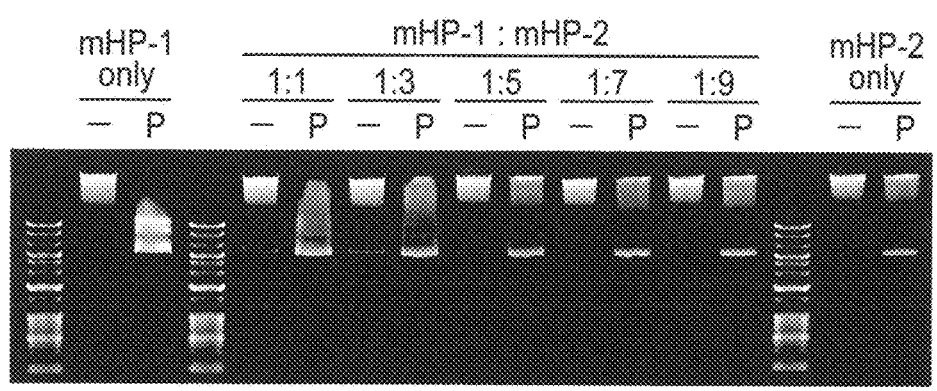
FIG. 11 is an electropherogram showing test results of Example 7.

The results are shown in FIG. 11. FIG. 11 is a photograph showing the agarose gel subjected to UV irradiation. Of two lanes indicated by the respective samples, the left lane indicates the results of a PGA (−) sample (sample for the condensability evaluation) and the right lane for those of a PGA (+) sample (sample for the dissociation evaluation). When an integrated band with a large molecular weight, which strongly shines is observed in the left lane, it was evaluated as a high condensability. When a band which strongly shines in a region of a molecular weight of 5 to 7 kbp was observed in the right lane, it was estimated as a high dissociation. From the results of FIG. 11, the peptide-nucleic-acid complexes produced by mixing mHP-1 and mHP-2 exhibited a reduced dissociation as compared to the case of mHP-1 being used solely. Further, they showed a high condensability as compared to the case of mHP-2 being used solely. Thus, it has been suggested that when both of mHP-1 and mHP-2 are included, a high condensability can be obtained, and when mHP-1 or mHP-2 is used solely, a middle dissociation can be obtained. In particular, the cases where the mixture ratio between mHP-1 and mHP-2 was 1:1 to 1:5 exhibited excellent results.

Example 8

The encapsulation of nucleic acid into the liposome by the peptide of the embodiment was evaluated.

COATSOME/SS-20 (Nippon Oil & Fats), DOPE, cholesterol and DMG-PEG were dissolved into ethanol at a molar ratio of 5:3:1:0.3, to obtain a lipid solution. Five sets of 50 µL of lipid solutions put into tubes were prepared, and 50 µL of peptide-nucleic-acid solutions (1) to (4) and (7) of Example 6 were dropped thereto while stirring each lipid solution, thereby forming liposomes. 400 µL of 10 mM-HEPES (pH: 5.4) was added to each of the liposome solutions to make a total amount of 500 µL (this liposome solution will be referred to as "Complex" hereinafter).

The average particle diameter, polydispersity index and Zeta potential of liposome were investigated using the Complex. The average particle diameter, polydispersity index and Zeta potential were measured using a zetasizer.

The results are shown in Table 6.

TABLE 6

| No. | Peptide mixture ratio (mHP-1:mHP-2) | Average particle diameter (zAve · nm) | Polydispersity index (PDI) | Zeta potential (mV) |
|---|---|---|---|---|
| 1 | 1:0 | 244.7 | 0.193 | 31.6 |
| 2 | 1:1 | 231.2 | 0.194 | 34.0 |
| 3 | 1:3 | 250.6 | 0.228 | 34.6 |
| 4 | 1:5 | 243.8 | 0.222 | 39.1 |
| 7 | 0:1 | 250.0 | 0.092 | 36.2 |

The results of Table 6 indicated that in any samples, the average particle diameter was around 230 to 250 nm, the PDI was 0.3 or less and the Zeta potential value was around 35 mV. From the results, it has been found that regardless of the mixture ratio between mHP-1 and mHP-2, the liposomes were formed homogeneously.

Example 9

The encapsulation of nucleic acid to the liposome by the peptide of the embodiment was evaluated by measuring the amount of encapsulation of the nucleic acid by the liposome. The amount of nucleic acid encapsulated in liposome was measured using an AccuBlue (registered trademark) dsDNA quantification kit.

Using the Complexes produced in Example 8, liposome solutions (which will be referred to as "HEPES replacement") in which ethanol, which is the solvent of Complex is substituted by HEPES were produced. The HEPES replacements were produced by adding 400 µl of 10 mM-HEPES (pH: 5.4) to 400 µL of each solution of Complex and condensing each to 200 µl with an ultrafiltration film for 300 kDa, and further adding 2.1 ml of 10 mM-HEPES (pH: 7.3), followed by ultrafiltration, thus substituting the solvent and finally condensing to 100 µL.

As samples for quantifying the entire nucleic acid, five sets of 8 µL of 10 mM-HEPES (pH: 7.3) were prepared and 1 µL of the respective HEPES substitutes and 1.0 µL of Triton-X100 (registered trademark (the final concentration: 1%)), which cleaves the liposomes, were added to prepare mixtures. As samples for quantifying the unencapsulated nucleic acid, five sets of 9 µL of 10 mM-HEPES (pH: 7.3) were prepared and 1 of the respective HEPES substituents were added thereto to prepare mixtures. After they were let stand still for 10 minutes at room temperature, the AccuBlue quantification liquid was added to each sample and well mixed. Then, the nucleic acid concentration of each sample was measured with a fluorescence microplate reader.

The results are shown in FIGS. 12 and 13. FIG. 12 indicates the amount of nucleic acid in each sample for quantification of the unencapsulated nucleic acid. FIG. 13 indicates the nucleic acid encapsulation rate in each liposome calculated by dividing of the numerical value obtained by subtracting the amount of nucleic acid in a sample for quantification of the unencapsulated nucleic acid from the amount of nucleic acid in a sample for quantification of the entire nucleic acid, by the amount of the nucleic acid in the sample for quantification of nucleic acid. The results of FIGS. 12 and 13 indicate that the liposomes produced from a peptide solution in which mHP-1 and mHP-2 was mixed by a ratio of 1:3 or higher exhibited a reduced amount of unencapsulated nucleic acid, thereby achieving an improved nucleic acid encapsulation rate. Thus, it has been suggested from this that with a mixture having a mixture ratio between mHP-1 and mHP-2 of 1:3 or higher, the nucleic acid condensing is improved and more nucleic acid is encapsulated by liposome. In addition, from the above-described test results and those shown in Table 6 of Example 8, it has been clarified that when using both mHP-1 and mHP-2, a nucleic acid delivery carrier which has an appropriate average particle diameter and Zeta potential can be produced despite the fact that it includes more nucleic acid.

Example 10

The transfection degree of nucleic acid into a cell by the liposome in which the nucleic acid was encapsulated by the peptide of the embodiment was evaluated.

As nucleic acid to be encapsulated in the liposome, pAmp-CMV-nLuc was used. The pAmp-CMV-nLuc is a reporter vector which contains a NanoLuc gene as the reporter gene. The pAmp-CMV-nLuc includes a CMV promoter as a gene expression promoter, and in its lower stream, a NanoLuc gene, IRES sequence and a replication initiation protein (LT, large T antigen) gene of simian virus 40 (SV40) which are liked in this order, and further, in a lower stream, a replication initiation sequence (SV40 ori) of SV40. Using the nucleic acid, liposome solutions were produced by methods similar to those of Examples 8 and 9.

The liposome solution produced as above was added to a human acute T-cell lymphoma-originated cell strain (Jurkat). As the culture medium to culture Jurkat, a culture medium in which fetal calf serum was added by 10% to RPMI1640 was used. After the culturing, Jurkat was peeled off from the bottom surface of the culture medium using 0.05%-trypsin EDTA and then the cells were collected by centrifuge at 200×g for 3 minutes. After that, a fresh culture medium was used to adjust the number of cells to $5.0 \times 10^5$ cells/mL. To 200 μL of the cell suspension, 10 μL of the above-described liposome solution was added and mixed gently. Then, the cells were further cultured under a 5% —$CO_2$ atmosphere at 37 degrees Celsius.

48 hours after the addition of the liposome, a luminescence substrate (Nano-Glo Luciferase Assay Substrate and Promega) was added to the culture medium to dilute to 1/2000. This culture dish was set to LV200 (a luminescence imaging system of Olympus) and photographed. The shooting conditions were as follows: object-glass magnification: ×20, imaging lens magnification: ×0.2, exposure time: 3 min, EM Gain: 610. The control of LV200 and Image MEX and the image processing of the shot images were carried out by Meta Morph (Molecular Device).

The luminescence intensity of the cells in which the nucleic acid was transfected and the reporter gene was expressed was detected using the cell photographs. The luminescence intensity was detected by NIS-Elements D (Nikon).

The results are shown in FIG. 14. The results of FIG. 14 indicate that liposomes produced from a peptide solution having a mixture ratio between mHP-1 and mHP-2 of 1:1 to 1:5 increased the luminescence intensity of the cells as compared to the cases where a peptide mHP-1 or mHP-2 was used solely. It has been suggested from this that when the mixture ratio between mHP-1 and mHP-2 is 1:1 to 1:5, a great amount of nucleic acid is delivery to a cell and a great amount of the delivered nucleic acid is expressed.

From the test results above, it has been clarified that when mHP-1 and mHP-2 are mixed, the nucleic acid condensability is improved and the nucleic acid is efficiently encapsulated in liposome, a great amount of nucleic acid can be transfected into a cell more efficiently by the method of delivering the nucleic acid to a cell of the embodiment using the liposome, and the nucleic acid delivered to the cell by the method is expressed more efficiently. The reasons for obtaining such results are considered as the followings. That is, as indicated by the test results shown in FIG. 11 of Example 7, for example, samples using both mHP-1 and mHP-2 exhibit high condensability, and middle dissociation between those of mHP-1 and mHP-2. Therefore, in the presence of mHP-2, more nucleic acid is encapsulated by liposome than in the case of using mHP-1 solely, and then after the nucleic acid delivery carrier is delivered to the cell, nucleic acid is dissociated more efficiently in the presence of mHP-1 than the case of using mHP-2 solely. Therefore, more nucleic acids are delivered to a cell and they are more efficiently expressed.

Example 11

The condensability of nucleic acid by the peptide of the embodiment and the dissociation of the peptide and nucleic acid was evaluated by a gel retardation assay.

Three kinds of peptides shown in Table 7, namely, mHP-1, mHP-2 and M9 were produced.

TABLE 7

| | Sequences | SEQ ID NO. | Number of residual amino acids |
|---|---|---|---|
| mHP-1 | RQRQRYYRQRQRGGRRRRRR | 1 | 20 |
| mHP-2 | RRRRRRYYRQRQRGGRRRRRR | 3 | 21 |
| M9 | GNQSSNFGPMKGGNFGGRSSGPYGGGGQ YFAKPRNQGGYGGGKCRGKVPGKYGKG | 6 | 55 |

Each of the peptides was dissolved in 10 mM-HEPES (pH: 5.4) and several peptide solutions having different peptide concentrations were prepared.

For M9, one peptide solution was prepared to have a peptide concentration of: (1) 0.24 mg/ml. For mHP-1 and mHP-2, peptide solutions were prepared to have a peptide concentration of 0.24 mg/ml and a mixture ratio between mHP-1 and mHP-2 of 1:3, and 1 μL of M9 was added to one to prepare a peptide solution (2), and M9 was not added to one to prepare a peptide solution (3). Moreover, the plasmid vector (pDNA) was diluted with purified water to prepare a nucleic acid solution having a pDNA concentration of 0.15 mg/ml.

The peptide solutions (1) to (3) (100 μL) were prepared in tubes and the nucleic acid solution (200 μL) was dropped and mixed thereto while stirring each solution to condense the nucleic acids, and thus peptide-nucleic-acid complexes were obtained.

As samples for the condensability evaluation, five sets of 5.5 μL of 10 mM-HEPES (pH: 5.4) were prepared, and 4.5 μL of the respective peptide-nucleic-acid solutions described above were added to prepare mixtures. As samples for the dissociation evaluation, five sets of 4.5 μL of 10 mM-HEPES (pH: 5.4) were prepared and 4.5 μL of the respective peptide-nucleic-acid solutions described above and 1.0 μL of a poly-glutamic-acid (PGA) solution were added thereto to prepare mixtures. After they were let stand still for 10 minutes at room temperature, 1.0 μL of an electrophoretic buffer (50%-sucrose solution) was added to each mixture, and they were mixed well, to carry out electrophoresis with a 0.8%-agarose gel. After the electrophoresis, the nucleic acid dyed with ethidium bromide was visualized by UV irradiation, and the nucleic acids condensed by the peptide and the nucleic acid dissociating with the peptide and moving into the gel were detected.

Figure 15:
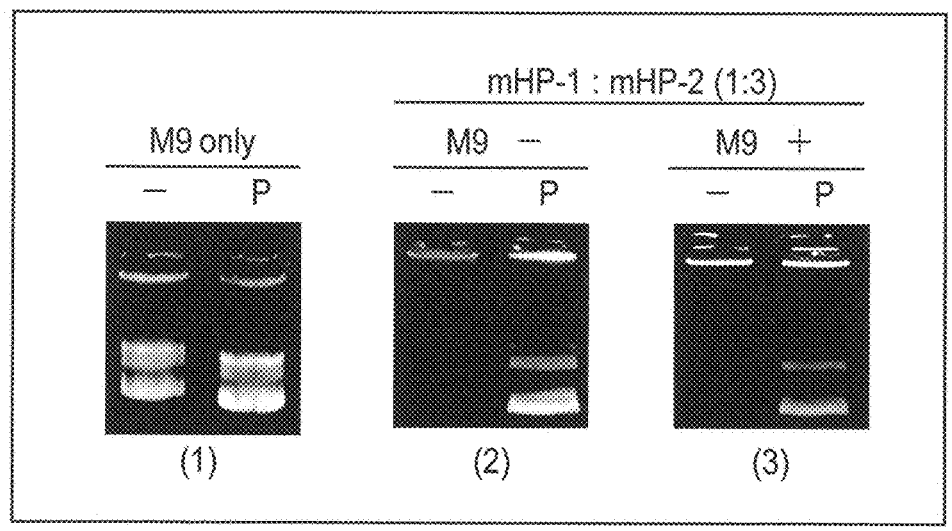
FIG. 15 is an electropherogram showing test results of Example 11.

The results are shown in FIG. 15. FIG. 15 is a photograph showing the agarose gel subjected to UV irradiation. Of two lanes indicated by the respective samples, the left lane indicates the results of a PGA (−) sample (sample for the condensability evaluation) and the right lane for those of a PGA (+) sample (sample for the dissociation evaluation). When an integrated band with a large molecular weight, which strongly shines is observed in the left lane, it was evaluated as a high condensability. When two bands which shine strongly in a region of a molecular weight of 5 to 10 kbp were observed in the right lane, it was estimated as high dissociation. From the results of FIG. 15, it has been suggested that M9 when used solely does not exhibit nucleic acid condensability, or does not influence the condensability or dissociation of nucleic acid by a peptide solution in which mHP-1 and mHP-2 were mixed.

Example 12

The condensability of the nucleic acid by the peptide of the embodiment and the potential of the peptide-nucleic-acid complexes were evaluated.

The peptide-nucleic-acid complexes were investigated in terms of average particle diameter, polydispersity index and Zeta potential using the peptide-nucleic-acid solutions (2) and (3) produced in Example 11. The average particle diameter, polydispersity index and Zeta potential were measured using a zetasizer.

The results are shown in Table 8.

TABLE 8

| | Average particle diameter (zAve · nm) | Polydispersity index (PDI) | Zeta potential (mV) |
|---|---|---|---|
| M9 (−) | 145.2 | 0.128 | −34.7 |
| M9 (+) | 191.1 | 0.196 | −26.7 |

The results of Table 8 indicate that the peptide-nucleic-acid complex produced by adding M9 thereto exhibited about 50 nm larger average particle diameter as compared to the case where M9 was not added, but both of the samples showed a PDI of 0.3 or less. Thus, it has been found that when M9 was added, the particle diameter of the complex increases slightly, homogeneous particles are formed. Moreover, it has been also found that in any sample, the Zeta potential value is around −30 mV, and a complex having such a charge which make it easy to be encapsulated in liposome can be formed.

Example 13

The encapsulation of the nucleic acid into liposome by the peptide of the embodiment was evaluated.

COATSOME/SS-20 (Nippon Oil & Fats), DOPE, cholesterol and DMG-PEG were dissolved into ethanol at a molar ratio of 5:3:1:0.3, and thus a lipid solution was obtained. Five sets of 50 μL of lipid solutions put into tubes were prepared, and 50 μL of peptide-nucleic-acid solutions (2) and (3) of Example 11 were dropped thereto while stirring each lipid solution, thereby forming liposomes. 400 μL of 10 mM-HEPES (pH: 5.4) was added to each of the liposome solutions to make a total amount of 500 μL (this liposome solution will be referred to as "Complex" hereinafter).

The liposomes were investigated in terms of average particle diameter, polydispersity index and Zeta potential using the Complex. The average particle diameter, polydispersity index and Zeta potential were measured using a zetasizer.

The results are shown in Table 9.

TABLE 9

| | Average particle diameter (zAve · nm) | Polydispersity index (PDI) | Zeta potential (mV) |
|---|---|---|---|
| M9 (−) | 237.5 | 0.104 | 44.0 |
| M9 (+) | 210.3 | 0.122 | 45.2 |

The results of Table 9 indicate that the average particle diameter of the liposomes produced from the peptide solution to which M9 was added was smaller than those of (around 230 nm to 250 nm) of the liposomes produced above by the method. On the other hand, the average particle diameter of the liposomed produced using the peptide solution to which M9 was not added was within the range of the average particle diameters of the liposomes described above. Moreover, in both samples, the PDI was 0.3 or less and the Zeta potential was around 45 mV. It has been found from this that when M9 is added to a peptide solution, liposomes with small particle diameters are homogenously formed.

Example 14

The transfection degree of nucleic acid into a cell by the liposome in which the nucleic acid was encapsulated by the peptide of the embodiment was evaluated.

As nucleic acid to be encapsulated in the liposome, pAmp-CMV-nLuc was used. The pAmp-CMV-nLuc is a reporter vector which contains a NanoLuc gene as the reporter gene. The pAmp-CMV-nLuc includes a CMV promoter as a gene expression promoter, and in its lower stream, a NanoLuc gene, IRES sequence and a replication initiation protein (LT, large T antigen) gene of simian virus 40 (SV40) which are liked in this order, and further, in a lower stream, a replication initiation sequence (SV40 ori) of SV40. Using the nucleic acid, Complexes were produced by method similar to that of Example 13. Further, liposome solutions (which will be referred to as "HEPES replacement") in which ethanol, which is the solvent of Complex is substituted by HEPES were produced. The HEPES replacements were produced by adding 400 μl of 10 mM-HEPES (pH: 5.4) to 400 μL of each solution of Complex and condensing each to 200 μl with an ultrafiltration film for 300 kDa, and further adding 2.1 ml of 10 mM-HEPES (pH: 7.3), followed by ultrafiltration, thus substituting the solvent and finally condensing to 100 μL.

The liposome solutions produced as above were added to a human acute T-cell lymphoma-originated cell strain (Jurkat). As the culture medium to culture Jurkat, a culture medium in which fetal calf serum was added by 10% to RPMI1640 was used. After the culturing, Jurkat was peeled off from the bottom surface of the culture medium using 0.05% of trypsin-EDTA and then the cells were collected by centrifuge at 200×g for 3 minutes. After that, a fresh culture medium was used to adjust the number of cells to $5.0 \times 10^5$ cells/mL. To 200 μL of the cell suspension, 10 μL of the above-described liposome solution was added and mixed gently. Then, the cells were further cultured under a 5%-$CO_2$ atmosphere at 37 degrees Celsius.

48 hours after the addition of the liposome, a luminescence substrate (Nano-Glo Luciferase Assay Substrate and Promega) was added to the culture medium to dilute to 1/2000. This culture dish was set to LV200 (a luminescence imaging system of Olympus) and photographed. The shooting conditions were as follows: object-glass magnification: ×20, imaging lens magnification: ×0.2, exposure time: 3 min, EM Gain: 610. The control of LV200 and Image MEX and the image processing of the shot images were carried out by Meta Morph (Molecular Device).

The luminescence intensity of the cells in which the nucleic acid was transfected and the reporter gene was expressed was detected using the cell photographs. The luminescence intensity was detected by NIS-Elements D (Nikon).

The results are shown in FIG. 16. The results of FIG. 16 indicate that the liposome produced using the peptide to which M9 was added exhibited a high cell luminescence intensity as compared to the case where M9 was not added. It has been suggested from this fact that when the peptide to which M9 was added is used, a great amount of nucleic acid is delivered to a cell and a great amount of delivered nucleic acid is expressed. One reason for this result is considered that with addition of M9, the liposomes are downsized, thereby increasing the amount of nucleic acid delivery to a cell and increasing the luminescence intensity as indicated by the results of Example 13.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

```
                         SEQUENCE LISTING

<110>  Kabushiki Kaisha Toshiba
<120>  Nucleic acid condensing peptide, Nucleic acid condensing
       peptide set, nucleic acid delivery carrier, nucleic acid
       delivery method, cell production method, cell detection
       method and kit
<130>  17S02195
<140>  PCT/IB2017/057317
<141>  2017 Nov. 22
<150>  JP 2016-226895
<151>  2016 Nov. 22
<150>  JP 2017-178206
<151>  2017 Sep. 15
<160>  6
<170>  PatentIn version 3.5

<210>  1
<211>  20
<212>  PRT
<213>  Artificial Sequence
<220>
<223>  Nucleic acid condensing peptide
<400>  1
Arg Gln Arg Gln Arg Tyr Tyr Arg Gln Arg Gln Arg Gly Gly Arg Arg
1               5                   10                  15

Arg Arg Arg Arg
            20

<210>  2
<211>  13
<212>  PRT
<213>  Artificial Sequence
<220>
<223>  Nucleic acid condensing peptide
<400>  2
Arg Gln Arg Gln Arg Gly Gly Arg Arg Arg Arg Arg Arg
1               5                   10

<210>  3
<211>  21
<212>  PRT
<213>  Artificial Sequence
<220>
<223>  Comparative example of nucleic acid condensing peptide
<400>  3
Arg Arg Arg Arg Arg Arg Tyr Tyr Arg Gln Arg Gln Arg Gly Gly Arg
1               5                   10                  15

Arg Arg Arg Arg Arg
            20

<210>  4
<211>  14
```

-continued

```
                            SEQUENCE LISTING

<212> PRT
<213> Artificial Sequence
<220>
<223> Comparative example of nucleic acid condensing peptide
<400>   4
Arg Arg Arg Arg Arg Gly Gly Arg Arg Arg Arg Arg Arg
1               5                   10

<210>   5
<211>  32
<212> PRT
<213> salmon
<400>   5
Pro Arg Arg Arg Arg Ser Ser Ser Arg Pro Ile Arg Arg Arg Pro
1               5                   10                  15

Arg Arg Ala Ser Arg Arg Arg Arg Arg Gly Gly Arg Arg Arg Arg
                20                  25                  30

<210>   6
<211>  39
<212> PRT
<213> human
<400>   6
Gly Asn Gln Ser Ser Asn Phe Gly Pro Met Lys Gly Gly Asn Phe Gly
1               5                   10                  15

Gly Arg Ser Ser Gly Pro Tyr Gly Gly Gly Gln Tyr Phe Ala Lys
                20                  25                  30

Pro Arg Asn Gln Gly Gly Tyr
        35
```

```
                            SEQUENCE LISTING

<160> NUMBER OF SEQ ID NOS: 6

<210> SEQ ID NO 1
<211> LENGTH: 20
<212> TYPE: PRT
<213> ORGANISM: Artificial Sequence
<220> FEATURE:
<223> OTHER INFORMATION: Nucleic acid condensing peptide

<400> SEQUENCE: 1

Arg Gln Arg Gln Arg Tyr Tyr Arg Gln Arg Gln Arg Gly Gly Arg Arg
1               5                   10                  15

Arg Arg Arg Arg
            20

<210> SEQ ID NO 2
<211> LENGTH: 13
<212> TYPE: PRT
<213> ORGANISM: Artificial Sequence
<220> FEATURE:
<223> OTHER INFORMATION: Nucleic acid condensing peptide

<400> SEQUENCE: 2

Arg Gln Arg Gln Arg Gly Gly Arg Arg Arg Arg Arg Arg
1               5                   10

<210> SEQ ID NO 3
<211> LENGTH: 21
<212> TYPE: PRT
<213> ORGANISM: Artificial Sequence
<220> FEATURE:
<223> OTHER INFORMATION: Comparative example of nucleic acid condensing
      peptide
```

```
<400> SEQUENCE: 3

Arg Arg Arg Arg Arg Arg Tyr Tyr Arg Gln Arg Gln Arg Gly Gly Arg
1               5                   10                  15

Arg Arg Arg Arg Arg
            20

<210> SEQ ID NO 4
<211> LENGTH: 14
<212> TYPE: PRT
<213> ORGANISM: Artificial Sequence
<220> FEATURE:
<223> OTHER INFORMATION: Comperative example of nucleic acid condensing
      peptide

<400> SEQUENCE: 4

Arg Arg Arg Arg Arg Arg Gly Gly Arg Arg Arg Arg Arg Arg
1               5                   10

<210> SEQ ID NO 5
<211> LENGTH: 32
<212> TYPE: PRT
<213> ORGANISM: salmon

<400> SEQUENCE: 5

Pro Arg Arg Arg Arg Ser Ser Ser Arg Pro Ile Arg Arg Arg Arg Pro
1               5                   10                  15

Arg Arg Ala Ser Arg Arg Arg Arg Arg Gly Gly Arg Arg Arg Arg
            20                  25                  30

<210> SEQ ID NO 6
<211> LENGTH: 39
<212> TYPE: PRT
<213> ORGANISM: human

<400> SEQUENCE: 6

Gly Asn Gln Ser Ser Asn Phe Gly Pro Met Lys Gly Gly Asn Phe Gly
1               5                   10                  15

Gly Arg Ser Ser Gly Pro Tyr Gly Gly Gly Gly Gln Tyr Phe Ala Lys
            20                  25                  30

Pro Arg Asn Gln Gly Gly Tyr
            35
```

What is claimed is:

1. A nucleic acid condensing peptide comprising:
   a first sequence RRRRRR at one terminal, a second sequence RQRQR at another terminal,
   none or one or more intermediate sequences comprising RRRRRR or RQRQR between the first sequence and the second sequence, and
   two or more neutral amino acids between two adjacent sequences of the first sequence, the second sequence and the intermediate sequence.

2. The peptide of claim 1, wherein the neutral amino acids contain G or Y.

3. The peptide of claim 1, wherein a full length of the peptide is 55 or less amino acids.

4. The peptide of claim 1, wherein the R is contained at a rate of 45% or higher to the entire sequence.

5. The peptide of claim 1, wherein the peptide is composed of salts containing sulfate ion.

6. The peptide of claim 1, wherein a sequence of the peptide is RQRQRYYRQRQRGGRRRRRR or RQRQRGGRRRRRR.

7. A peptide set for condensing nucleic acid, comprising:
   the nucleic acid condensing peptide of claim 1, as a first nucleic acid condensing peptide; and a second nucleic acid condensing peptide and/or a third nucleic acid condensing peptide,
   wherein the second nucleic acid condensing peptide comprises: a third sequence RRRRRR at one terminal, a fourth sequence RRRRRR at another terminal, none or one or more intermediate sequences comprising RRRRRR or RQRQR between the third sequence and the fourth sequence, and two or more neutral amino acids between two adjacent sequences of the third sequence, the fourth sequence and the intermediate sequence; and
   the third nucleic acid condensing peptide comprises an amino acid sequence GNQSSNFGPMKGGNFGGRSSGPYGGGGQYFAKPRNQGGY.

8. The peptide set of claim 7, wherein an amino acid sequence of the second nucleic acid condensing peptide is RRRRRRYYRQRQRGGRRRRRR.

9. The peptide set of claim 7, wherein an arbitrary amino acid sequence is linked to one end of the third nucleic acid condensing peptide.

10. The peptide set of claim 9, wherein the arbitrary amino acid sequence is an amino acid sequence which binds to the nucleic acid.

11. The peptide set of claim 7, wherein
when the peptide set comprises comprising the third nucleic acid condensing peptide, the first nucleic acid condensing peptide and/or the second nucleic acid condensing peptide are linked to the third nucleic acid condensing peptide.

12. A nucleic acid delivery carrier comprising:
a complex comprising the nucleic acid condensing peptide of claim 1 and a nucleic acid; and a liposome, wherein the complex is encapsulated in the liposome.

13. A nucleic acid delivery carrier comprising:
a complex comprising the nucleic acid condensing peptide set of claim 7 and a nucleic acid; and a liposome, wherein the complex is encapsulated in the liposome.

14. The nucleic acid delivery carrier of claim 12, further comprising: a function improving agent, wherein the function improving agent is encapsulated in the liposome, and wherein the function improving agent is at least one selected from the group consisting of:
a reagent for detecting a signal from a reporter gene;
a drug; and
a transcription promoter.

15. A nucleic acid delivery method comprising:
preparing the nucleic acid delivery carrier of claim 12; and
bringing the nucleic acid delivery carrier into contact with a cell, thereby delivering the nucleic acid into the cell.

16. The method of claim 15, wherein the cell is a cell in a living body.

17. The method of claim 15, further comprising: opening a pore in a cell membrane of the cell before or after bringing the nucleic acid delivery carrier and the cell into contact with each other.

18. The method of claim 17, wherein the opening the pore is carried out by applying voltage or ultrasonic waves to the cell.

19. A method of transforming a cell, comprising:
executing the nucleic acid delivery method of claim 15;
culturing the cell obtained; and
selecting a cell into which the nucleic acid is transfected into of the cells.

20. A cell detection method comprising:
executing the nucleic acid delivery method of claim 15, wherein the nucleic acid comprises a reporter gene expression cassette containing a reporter gene; and
detecting a signal from the reporter gene.

21. A kit comprising: the nucleic acid delivery carrier of claim 12; and a function improving agent, wherein the function improving agent is at least one selected from the group consisting of:
a reagent for detecting a signal from a reporter gene;
a drug; and
a transcription promoter.

22. The kit of claim 21, wherein
the kit is a kit for detecting a cell, the nucleic acid contained in the nucleic acid delivery carrier contains a reporter gene expression cassette for expressing a reporter gene, and the function improving agent contains the reagent for detecting a signal from the reporter gene.

23. The kit of claim 21, wherein the kit is a kit for modifying a function of a cell taken out of an organism. the nucleic acid contained in the nucleic acid delivery carrier contains a gene for modifying the function of the cell, and the function improving agent is a drug that promotes differentiation.

24. The kit of claim 21, wherein
the kit is a kit for killing a cell, the nucleic acid contained in the nucleic acid delivery carrier contains a gene which leads the cell to apoptosis, and the function improving agent contains actinomycin-D, cisplatin, bendamustine hydrochloride, betulic acid or a combination of any of these.

25. The kit of claim 21, wherein
the kit is a kit for producing a substance in a cell, the nucleic acid contained in the nucleic acid delivery carrier contains a gene for producing a desired substance in the cell, and the function improving agent contains a transcription promoter.

26. The peptide of claim 1, wherein the neutral amino acids contain two to five amino acids.

27. The peptide of claim 7, wherein the neutral amino acids contain G or Y.

28. The peptide of claim 7, wherein a full length of the peptide is 55 or less amino acids.

29. The peptide of claim 7, wherein the R is contained at a rate of 45% or higher to the entire sequence.

30. The peptide of claim 7, wherein the peptide is composed of salts containing sulfate ion.

31. The peptide of claim 7, wherein a sequence of the peptide is RQRQRYYRQRQRGGRRRRRR or RQRQRGGRRRRRR.

32. The peptide of claim 7, wherein the neutral amino acids contain two to five amino acids.

33. The peptide of claim 12, wherein the neutral amino acids contain G or Y.

34. The peptide of claim 12, wherein a full length of the peptide is 55 or less amino acids.

35. The peptide of claim 12, wherein the R is contained at a rate of 45% or higher to the entire sequence.

36. The peptide of claim 12, wherein the peptide is composed of salts containing sulfate ion.

37. The peptide of claim 12, wherein a sequence of the peptide is RQRQRYYRQRQRGGRRRRRR or RQRQRGGRRRRRR.

38. The peptide of claim 12, wherein the neutral amino acids contain two to five amino acids.

39. The peptide of claim 13, wherein the neutral amino acids contain G or Y.

40. The peptide of claim 13, wherein a full length of the peptide is 55 or less amino acids.

41. The peptide of claim 13, wherein the R is contained at a rate of 45% or higher to the entire sequence.

42. The peptide of claim 13, wherein the peptide is composed of salts containing sulfate ion.

43. The peptide of claim 13, wherein a sequence of the peptide is RQRQRYYRQRQRGGRRRRRR or RQRQRGGRRRRRR.

44. The peptide of claim 13, wherein the neutral amino acids contain two to five amino acids.

* * * * *